United States Patent
Meier et al.

(10) Patent No.: US 11,560,532 B2
(45) Date of Patent: *Jan. 24, 2023

(54) DETERGENT COMPOSITION WITH CATECHOL METAL COMPLEX COMPOUND

(71) Applicant: Henkel AG & Co. KGaA, Duesseldorf (DE)

(72) Inventors: Frank Meier, Duesseldorf (DE); Mareile Job, Leverkusen (DE); Christian Kropf, Hilden (DE); Ulrich Pegelow, Duesseldorf (DE)

(73) Assignee: Henkel AG & Co. KGaA, Duesseldorf (DE)

(*) Notice: Subject to any disclaimer, the term of this patent is extended or adjusted under 35 U.S.C. 154(b) by 109 days.

This patent is subject to a terminal disclaimer.

(21) Appl. No.: 17/228,524

(22) Filed: Apr. 12, 2021

(65) Prior Publication Data

US 2021/0230513 A1 Jul. 29, 2021

Related U.S. Application Data

(63) Continuation of application No. PCT/EP2019/065984, filed on Jun. 18, 2019.

(30) Foreign Application Priority Data

Oct. 11, 2018 (DE) ................... 10 2018 217 393.1

(51) Int. Cl.

| | | |
|---|---|---|
| C11D 17/04 | (2006.01) | |
| C11D 17/06 | (2006.01) | |
| C11D 11/00 | (2006.01) | |
| C11D 1/83 | (2006.01) | |
| C11D 3/16 | (2006.01) | |
| C11D 3/40 | (2006.01) | |
| C07F 11/00 | (2006.01) | |
| C07F 13/00 | (2006.01) | |
| C07F 15/02 | (2006.01) | |
| C09B 57/10 | (2006.01) | |
| C11D 1/22 | (2006.01) | |
| C11D 1/29 | (2006.01) | |
| C11D 1/72 | (2006.01) | |

(52) U.S. Cl.
CPC ............ *C11D 3/168* (2013.01); *C07F 11/005* (2013.01); *C07F 13/005* (2013.01); *C07F 15/025* (2013.01); *C09B 57/10* (2013.01); *C11D 1/83* (2013.01); *C11D 3/40* (2013.01); *C11D 11/0017* (2013.01); *C11D 17/045* (2013.01); *C11D 1/22* (2013.01); *C11D 1/29* (2013.01); *C11D 1/72* (2013.01); *C11D 1/721* (2013.01)

(58) Field of Classification Search
None
See application file for complete search history.

(56) References Cited

U.S. PATENT DOCUMENTS

| | | |
|---|---|---|
| 10,876,076 B2 | 12/2020 | Kropf et al. |
| 2003/0125222 A1 | 7/2003 | Jahns et al. |
| 2009/0176684 A1 | 7/2009 | Gardner et al. |
| 2017/0240849 A1* | 8/2017 | Kropf ............... C11D 3/2093 |
| 2019/0169544 A1* | 6/2019 | Kropf ............... C11D 7/3263 |

FOREIGN PATENT DOCUMENTS

| | | | |
|---|---|---|---|
| EP | 1305432 B1 | 9/2010 | |
| GB | 1296839 A | 11/1972 | |
| WO | 9206165 A1 | 4/1992 | |
| WO | 9623873 A1 | 8/1996 | |
| WO | 9629397 A1 | 9/1996 | |
| WO | 9703160 A1 | 1/1997 | |
| WO | 9714804 A1 | 4/1997 | |
| WO | 9812307 A1 | 3/1998 | |
| WO | 0060060 A2 | 10/2000 | |
| WO | 0060063 A1 | 10/2000 | |
| WO | 0146700 A2 | 6/2001 | |
| WO | 0149817 A2 | 7/2001 | |
| WO | 0166712 A2 | 9/2001 | |
| WO | 0210356 A2 | 2/2002 | |
| WO | 02099091 A2 | 12/2002 | |
| WO | WO 2006/133773 A1 * | 12/2006 | |
| WO | WO 2006/133790 A1 * | 12/2006 | |
| WO | 2010043452 A1 | 4/2010 | |
| WO | WO 2010/072511 A2 * | 7/2010 | |

OTHER PUBLICATIONS

Meyer, M. et al, "Rearrangement Reactions in Dinuclear Triple Helicates," Inorg. Chem., 1997, vol. 36, pp. 5179-5191.*
PCT International Search Report & Written Opinion PCT/EP2019/065984 Completed: Sep. 30, 2019; dated Oct. 10, 2019 41 pages.
Karpishin, Timothy B. et al., "Stereoselectivity in Chiral FeIII and GaIII Tris(catecholate) Complexes Effected by Nonbonded, Weakly Polar Interactions", Journal of American Chemical Society, 1993, vol. 115, pp. 6115-6125.

(Continued)

*Primary Examiner* — Lorna M Douyon
(74) *Attorney, Agent, or Firm* — Bojuan Deng

(57) ABSTRACT

Catechol metal complex compounds of formula (I)

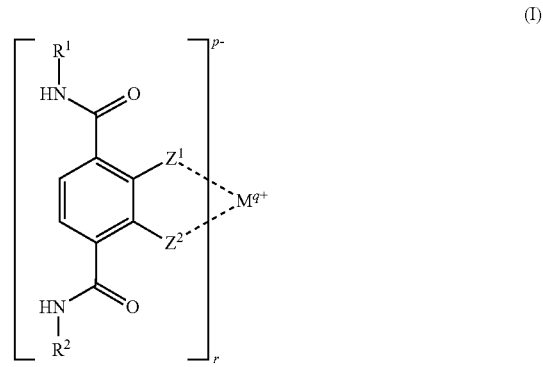

are colored and can be used to give color to surfactant compositions. Detergents containing these catechol metal complex compounds do not stain the textile even after repeated use.

18 Claims, No Drawings

(56) References Cited

OTHER PUBLICATIONS

Yin, Hang et al., "Terephthalamide Derivatives as Mimetics of Helical Peptides: Disruption of the Bcl-xL/Bak Interaction", Journal of American Chemical Society, 2005, vol. 127, pp. 5463-5468.
Clarke, Kristy M., et al., "A Bidentate Terephthalamide Ligand, TAMmeg, as an Entry Into Terephthalamide-Containing Therapeutic Iron Chelating Agents", Inorganic Chemistry, 2006, vol. 46, No. 6, XP-002794654.

\* cited by examiner

DETERGENT COMPOSITION WITH CATECHOL METAL COMPLEX COMPOUND

FIELD OF THE INVENTION

The present invention is in the technical field of detergent compositions, in particular for textiles, and relates in particular to the coloring of detergents. The present invention also relates to special catechol metal complex compounds, the production thereof and a method for textile treatment using said detergent composition.

BACKGROUND OF THE INVENTION

Aesthetics play an important role in liquid detergents, especially in transparent or translucent bottles or in pre-portioned products such as pouches. In particular, products having intense and strong colors are desired by the consumer. A risk when using new dyes and/or large amounts of dyes is that these dyes are absorbed onto the textile during the washing process and there is local or uniform discoloration. The effect can be measured in laboratory tests with the "staining tendency" and is also visually perceptible to the consumer. It may be that the washed garment is irreversibly damaged and the discoloration can no longer be removed even after washing again.

BRIEF SUMMARY OF THE INVENTION

The problem addressed by the present invention was therefore that of providing a detergent which, when stored, has an intense color and is color-stable, but does not discolor the textile in the washing process.

The inventors of the present invention have surprisingly found that this problem can be solved using special catechol metal complex compounds as a dye. The use of special catechol metal complex compounds reduces the risk of undesired textile staining, since said complex compounds have a very low affinity for natural and synthetic fabrics.

In addition, detergents having the catechol metal complex compounds according to the invention exhibit a good bleaching effect in the presence of an excess of free catechol ligands. The detergents are particularly advantageous in their cleaning effect against soiling that can only be removed by bleaching. This soiling is that containing polymerizable substances. The polymerizable substances are primarily polyphenolic dyes, preferably flavonoids, in particular from the class of anthocyanidins or anthocyanins. The soiling can in particular have been caused by food products or beverages that contain the corresponding dyes. The soiling can in particular be stains from fruits or vegetables or red wine stains, which in particular contain polyphenolic dyes, especially those from the class of anthocyanidins or anthocyanins.

DETAILED DESCRIPTION OF THE INVENTION

A first object of the invention is therefore a catechol metal complex compound of formula (I)

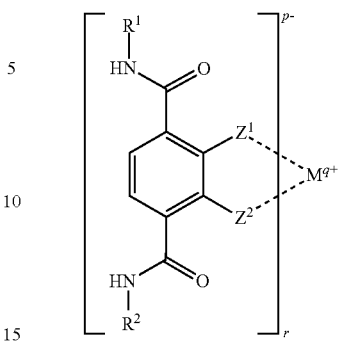

where
$R^1$ and $R^2$ independently represent a hydrocarbon group having 1 to 20 carbon atoms, which is optionally substituted by at least one group selected from hydroxy, $(C_1-C_4)$ alkoxy, $(C_1-C_4)$ alkoxy$(CH_2CH_2O)_n-$, $-NR'R''$ or $-N^+R'R''R'''X^-$, where n=1 to 10, R', R" and R'" independently represent H or a linear or branched aliphatic hydrocarbon group having 1 to 3, preferably 1 to 2 carbon atoms and $X^-$ represents an anion, $Z^1$ and $Z^2$ independently represent OH or $O^-$, M represents a metal cation of a transition metal or lanthanoid, q as the charge number of the metal cation M represents a number 2, 3 or 4, p as the charge number of the catechol ligand represents a number 0, 1 or 2, r represents a number 1, 2, 3 or 4.

"Liquid," as used herein in relation to detergents according to the invention, includes all detergents which are flowable under standard conditions (20° C., 1013 mbar) and in particular also includes gels and pasty compositions. In particular, the term also includes non-Newtonian liquids which have a yield point.

Unless otherwise indicated, all amounts indicated in connection with the constituents of the detergent described herein refer to wt. %, in each case based on the total weight of the composition. Moreover, such stated amounts that relate to at least one constituent always relate to the total amount of this type of constituent contained in the detergent, unless explicitly indicated otherwise. This means that such stated amounts, for example in connection with "at least one non-ionic surfactant," refer to the total amount of non-ionic surfactant contained in the detergent.

"At least one," as used herein, refers to one or more, for example 1, 2, 3, 4, 5, 6, 7, 8, 9 or more. In connection with constituents of the compositions described herein, this information does not refer to the absolute amount of molecules, but to the type of the constituent. "At least one non-ionic surfactant" therefore means, for example, one or more different non-ionic surfactants, i.e. one or more different types of non-ionic surfactants. Together with stated amounts, the stated amounts refer to the total amount of the correspondingly designated type of constituent, as defined above.

"Substantially free," as used herein, means that the particular compound is contained in the relevant component or composition in less than 0.01 wt. %, preferably 0.001 wt. %, more preferably 0.0001 wt. %, and most preferably not at all.

If compounds are described as substituted in the present invention, the possible substituents are known to a person skilled in the art. Particularly preferably, unless explicitly stated otherwise, the substituents are selected from —F, —Cl, —Br, —I, —OH, =O, —OR$^1$, —NH$_2$, —NHR$^1$, —NR$^1_2$ and —COOR$^1$, where R$^1$ is an alkyl group having 1 to 10 carbon atoms.

In complex chemistry, "ligand" refers to those molecules which, in the presence of a substance that acts as a central atom or central ion (e.g. metal ion), are bonded to this substance to form a complex. As a "free ligand" or "uncomplexed ligand," the ligand is present in an uncomplexed form, unbound without grouping around a central atom or central ion.

The catechol metal complex compounds of formula (I) can be present as complex cations (q>r·p), complex anion (q<r·p) or as a neutral complex (q=r·p). In the first case, the cationic charge of the complex cation is compensated for by a corresponding anion equivalent while maintaining electroneutrality, which is preferably selected from the preferred suitable anions for X$^-$ of formula (I) (vide infra). In the second case, the anionic charge of the complex cation is compensated for by a corresponding cation equivalent while maintaining electroneutrality.

The groups R$^1$ and R$^2$ according to formula (I) independently represent one such C$_1$-C$_{20}$ hydrocarbon group. The hydrocarbon groups having 1 to 20 carbon atoms in formula (I) can be linear or branched, saturated or unsaturated, cyclic or alicyclic or aromatic. Such groups are preferably selected from C$_1$-C$_{20}$ alkyl, C$_1$-C$_{20}$ alkenyl, C$_6$-C$_{20}$ aryl, alkyl aryl having a total of 7 to 20 carbon atoms (e.g. benzyl), which in each case is optionally substituted by at least one group selected from hydroxy, (C$_1$-C$_4$) alkoxy, (C$_1$-C$_4$) alkoxy (CH$_2$CH$_2$O)$_n$—, —NR'R" or —N$^+$R'R"R'"X$^-$, where n=1 to 10, R', R" and R'" independently represent H or a linear or branched aliphatic hydrocarbon group having 1 to 3, preferably 1 to 2 carbon atoms and X$^-$ represents an anion.

Preferred suitable catechol metal complex compounds of formula (I) are characterized in that in formula (I) the groups R$^1$ and R$^2$ independently represent an alkyl group, an alkoxyalkyl group, a hydroxyalkyl group, a hydroxyalkyloxyalkyl group, (N-hydroxyethyl)-aminoethyl, (N-methoxyethyl)-aminoethyl or (N-ethoxyethyl)-aminoethyl, or an aromatic group.

According to formula (I), preferred alkyl groups are linear (C$_1$-C$_{10}$) alkyl groups or branched (C$_3$-C$_{10}$) alkyl groups or C$_5$-C$_6$ cycloalkyl. Methyl, ethyl, n-propyl, isopropyl, n-butyl, sec-butyl, tert-butyl, iso-butyl, n-pentyl, iso-pentyl, neopentyl, hexyl are particularly preferred alkyl groups according to formula (I) (most preferably methyl, ethyl, n-propyl, isopropyl).

According to formula (I), preferred alkenyl groups are allyl, vinyl and butenyl.

Preferred alkoxyalkyl groups of formula (I) are methoxyethyl, methoxypropyl, (2-methoxy)-ethoxyethyl, ethoxyethyl, ethoxypropyl or (2-ethoxy)-ethoxyethyl.

According to formula (I), preferred hydroxyalkyl groups are 2-hydroxyethyl, 3-hydroxypropyl, 2-hydroxypropyl, 1,2-dihydroxypropyl.

Preferred hydroxyalkyloxyalkyl groups according to formula (I) are 2-hydroxyethoxyethyl.

The groups R$^1$ and R$^2$ of formula (I) particularly preferably independently represent methyl, ethyl, n-propyl, iso-propyl, n-butyl, sec-butyl, tert-butyl, isobutyl, n-pentyl, iso-pentyl, neopentyl, hexyl, allyl, butenyl, 2-hydroxyethyl, 2-hydroxypropyl, 3-hydroxypropyl, 1,2-dihydroxypropyl, 2-methoxyethyl, 2-ethoxyethyl, 2-methoxypropyl, 3-methoxypropyl, 2-ethoxypropyl, 3-ethoxypropyl, 2-(N-hydroxyethyl)-aminoethyl, 2-(N-methoxyethyl)-aminoethyl or 2-(N-ethoxyethyl)-aminoethyl, benzyl or phenyl.

It has proven to be particularly preferred if the groups R$^1$ and R$^2$ in formula (I) are the same. Most preferably, R$^1$ and R$^2$ represent methyl, ethyl, n-propyl, isopropyl, n-butyl, sec-butyl, tert-butyl, iso-butyl, n-pentyl, iso-pentyl, neopentyl, hexyl, 2-hydroxyethyl, 2-hydroxypropyl, 3-hydroxypropyl, 2-methoxyethyl, 2-ethoxyethyl, 2-methoxypropyl, 3-methoxypropyl, 2-ethoxypropyl, 3-ethoxypropyl. Methyl, ethyl, n-propyl, iso-propyl are extremely preferred groups for R$^1$ and R$^2$ of the catechol metal complex compounds of formula (I).

X$^-$ according to formula (I) is preferably selected from the group comprising lactate, citrate, tartrate, succinate, perchlorate, tetrafluoroborate, hexafluorophosphate, alkyl sulfonate, alkyl sulfate, hydrogen sulfate, sulfate, dihydrogen phosphate, hydrogen phosphate, phosphate, isocyanate, rhodanide, chloride, nitrate, bromide, hydrogen carbonate and carbonate and mixtures of at least two of these, it being possible to ensure the charge balance in the presence of polyvalent anions by the presence of a corresponding plurality of cationic backbones of general formula (I) or, where necessary, by the presence of additional cations such as sodium or ammonium ions.

The dashed lines according to formula (I) represent coordinative bonds of the ligand to the metal cation M.

Most preferred catechol compounds of formula (I) are the compounds of formulas (I-a) and/or (I-b)

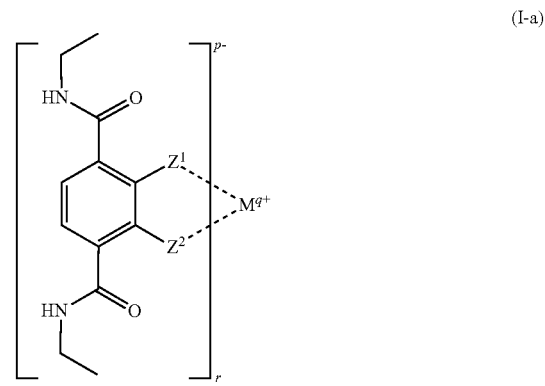

(I-a)

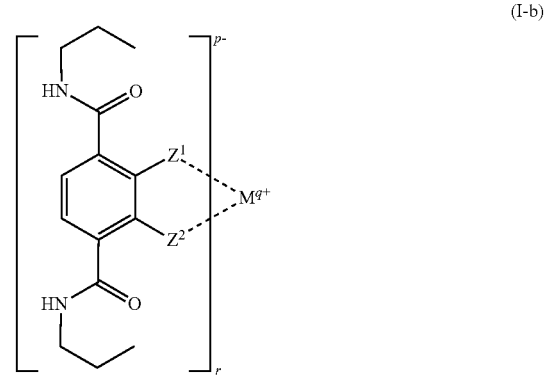

(I-b)

in which Z$^1$, Z$^2$, p, r, q and M are defined according to formula (I).

The catechol metal complex compounds of the present invention contain a metal ion M, which represents a metal cation of a transition metal or lanthanoid. A person skilled in the art understands a transition metal to be metals from the transition elements of the periodic table of elements according to the definition given in accordance with IUPAC rule 1-3.8.2 of inorganic chemistry. Lanthanoids are known to a person skilled in the art as lanthanum and the elements of the rare earth metals with atomic numbers 58 to 70 which follow lanthanum.

Preferred catechol metal complex compounds of formulas (I), (I-a) and (I-b) contain a metal cation M selected from Ti, Zr, Hf, V, Nb, Ta, Cr, Mo, W, Mn, Fe, Ru, Co, Ni, Cu, Zn, Ce, Sm or hydrates of these metal ions. Among these, those catechol metal complex compounds of formula (I) in which in formula (I) M is selected as the metal cation from a metal cation of Fe, Mn, Cr, Ni, Co, Ce, Cu or hydrates of these metal ions (in particular selected from Fe(II), Fe(III), Mn(II), Mn(IV), Ni(II), Co(II), Co(III), Ce(III), Cu(II) or hydrates of these metal ions) are particularly suitable.

The catechol metal complex compounds of formulas (I), (I-a) and (I-b) are colored. Preferred catechol metal complex compounds of formula (I) are characterized in that they absorb light in a wavelength of from 400 to 800 nm, measured by means of a UV-VIS spectrophotometer (e.g. Specord® S 600 with photodiode array from Analytik Jena AG) at a concentration of the complex of $10^{-5}$ mol/L in water at 20° C., a pH of 8 and a layer thickness of 1 cm.

The catechol metal complex compounds of formula (I) according to the invention can be provided by $0.1\tau$ mmol free ligand in the form of the corresponding catechol compound being dissolved in 10 ml methanol. $0.1\tau$ mmol KOH (as a 0.5M solution in methanol) is added thereto. 0.1 mmol of the metal chloride (r is as defined in formula (I) (vide supra)) is dissolved in 4 ml methanol, and this solution is added to the first solution. The mixture is stirred for one hour, the resulting solution is concentrated to 4 ml and 50 ml of diethyl ether is added. The precipitated metal complex is isolated by filtration.

A second object of the invention is a detergent, in particular a liquid detergent, containing, in each case based on the total weight of the detergent in a total amount of from 0.001 to 10.0 wt. %, preferably 0.01 to 3.0 wt. %, at least one catechol metal complex compound of formula (I)

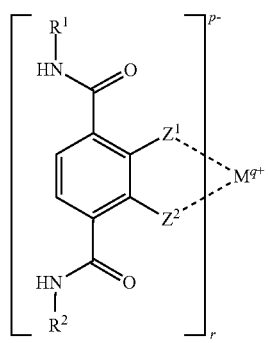

where
$R^1$ and $R^2$ independently represent a hydrocarbon group having 1 to 20 carbon atoms, which is optionally substituted by at least one group selected from hydroxy, $(C_1\text{-}C_4)$ alkoxy, $(C_1\text{-}C_4)$ alkoxy$(CH_2CH_2O)_n$—, —NR'R'' or —N$^+$R'R''R'''X$^-$, where n=1 to 10, R', R'' and R''' independently represent H or a linear or branched aliphatic hydrocarbon group having 1 to 3, preferably 1 to 2 carbon atoms and X$^-$ represents an anion, $Z^1$ and $Z^2$ independently represent OH or O$^-$, M represents a metal cation of a transition metal or lanthanoid, (in particular a metal cation from Ti, Zr, Hf, V, Nb, Ta, Cr, Mo, W, Mn, Fe, Ru, Co, Ni, Cu, Zn, Ce or Sm), q as the charge number of the metal cation M represents a number 2, 3 or 4, p as the charge number of the catechol ligand represents a number 0, 1 or 2, r represents a number 1, 2, 3 or 4, and at least one surfactant, preferably in a total amount of from 2 to 70 wt. %, in particular 10 to 65 wt. %, particularly preferably 15 to 60 wt. %.

The detergent according to the invention is preferably a liquid detergent. A substance (e.g. a composition) is liquid according to the definition of the invention if it is in the liquid state of matter at 20° C. and 1013 mbar.

The definitions introduced in the first object of the invention apply to the catechol complex compounds of formula (I). The preferred embodiments of the catechol metal complex compounds of formula (I) of the first object of the invention can also preferably be used in the detergent according to the invention.

The detergents according to the invention necessarily contain at least one surfactant.

The detergent according to the invention contains a total amount of from 0.1 to 70 wt. % of at least one surfactant. It is preferred according to the invention if the detergent contains, based on its total weight, a total amount of from 5 to 70 wt. %, preferably from 10 to 65 wt. %, particularly preferably from 12 to 60 wt. %, very particularly preferably from 15 to 60 wt. %, most preferably from 20 to 55 wt. %, of at least one surfactant. The following total surfactant amounts of the detergent according to the invention are also particularly preferably suitable:

10 to 70 wt. % or 12 to 70 wt. % or 15 to 70 wt. % or 20 to 70 wt. % or 5 to 65 wt. % or 10 to 65 wt. % or 12 to 65 wt. % or 15 to 65 wt. % or 20 to 65 wt. % or 5 to 60 wt. % or 10 to 60 wt. % or 12 to 60 wt. % or 15 to 60 wt. % or 20 to 60 wt. % or 5 to 55 wt. % or 10 to 55 wt. % or 12 to 55 wt. % or 15 to 55 wt. % or 20 to 55 wt. %.

The detergent according to the invention preferably contains at least one anionic surfactant. It is preferable for the anionic surfactant to be selected from the group consisting of $C_{8\text{-}18}$ alkylbenzene sulfonates, $C_{8\text{-}18}$ olefin sulfonates, $C_{12\text{-}18}$ alkane sulfonates, $C_{8\text{-}18}$ ester sulfonates, $C_{8\text{-}18}$ alkyl sulfates, $C_{8\text{-}18}$ alkenyl sulfates, fatty alcohol ether sulfates and mixtures thereof. Particularly preferably, the anionic surfactant is selected from at least one $C_{8\text{-}18}$ alkylbenzene sulfonate.

It has been found that these sulfonate and sulfate surfactants are particularly well suited for preparing stable liquid detergents.

It is preferred according to the invention for the detergent to contain at least one anionic surfactant of formula (T1)

in which
$R^1$ represents a linear or branched, substituted or unsubstituted group, selected from $C_{8\text{-}18}$ alkyl, aryl or $C_{8\text{-}18}$ alkyl aryl groups and the grouping -A- represents a chemical bond or a group —$(OZ)_n$—O—,
in which OZ represents an ethylene oxide (EO) or propylene oxide (PO) grouping and n represents an integer from 1 to 50, preferably from 1 to 20 and in particular from 2 to 10, more particularly preferably 2, 3, 4, 5, 6, 7 or 8, $Y^+$ represents a monovalent cation or the n-th part of an n-valent cation.

According to the invention it has proved suitable for said detergent to contain at least one such surfactant of the above formula (T1), in which A according to formula (T1) represents the structural unit —$(OZ)_n$—O—,
where OZ represents an ethylene oxide (EO) grouping or propylene oxide (PO) grouping and n represents an integer from 1 to 50, preferably from 1 to 20 and in particular from 2 to 10, more particularly preferably 2, 3, 4, 5, 6, 7 or 8,
and $R^1$ according to formula (T1) represents a linear or branched, substituted or unsubstituted alkyl group. Alkyl ether sulfates of formula (T1-1) result therefrom

 (T1-1).

In this formula (T1-1), $R^1$ represents a linear or branched, substituted or unsubstituted alkyl group, preferably a linear, unsubstituted alkyl group, particularly preferably a fatty alcohol group. Preferred groups $R^1$ are selected from decyl, undecyl, dodecyl, tridecyl, tetradecyl, pentadecyl, hexadecyl, heptadecyl, octadecyl, nonadecyl, eicosyl groups and mixtures thereof, the representatives having an even number of C atoms being preferred. Particularly preferred groups $R^1$ are derived from $C_{12}$-$C_{18}$ fatty alcohols, for example from coconut fatty alcohol, tallow fatty alcohol, lauryl, myristyl, cetyl or stearyl alcohol or from $C_{10}$-$C_{18}$ oxo alcohols. $Y^+$ is as previously specified in formula (T1).

According to formula (T1-1), OZ represents an ethylene oxide (EO) grouping or propylene oxide (PO) grouping, preferably an ethylene oxide grouping. According to formula (I-1), the index n represents an integer from 1 to 50, preferably from 1 to 20, and in particular from 2 to 10. Very particularly preferably, n represents the numbers 2, 3, 4, 5, 6, 7 or 8. According to formula (T1-1), $Y^+$ represents a monovalent cation or the n-th part of an n-valent cation, with in this case the alkali metal ions including $Na^+$ or $K^+$ being preferred, with $Na^+$ being particularly preferred. Further cations $Y^+$ may be selected from $NH_4^+$, ½ $Zn^{2+}$, ½ $Mg^{2+}$, ½ $Ca^{2+}$, ½ $Mn^{2+}$, and mixtures thereof.

Detergents may contain at least one alkyl ether sulfate selected from fatty alcohol ether sulfates of formula (T1-2) as a compound of formula (T1) or as a compound of formula (T1-1)

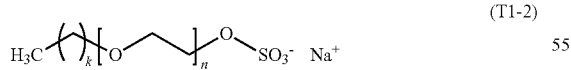 (T1-2)

where k=11 to 19, and n=2, 3, 4, 5, 6, 7 or 8. Very particularly preferred representatives are Na—$C_{12-14}$ fatty alcohol ether sulfates having 2 EO (k=11-13, n=2 in formula A-1). The degree of ethoxylation indicated represents a statistical average that can correspond to an integer or a fractional number for a specific product. The degrees of alkoxylation indicated represent statistical averages that can correspond to an integer or a fractional number for a specific product. Preferred alkoxylates/ethoxylates have a narrowed homolog distribution (narrow range ethoxylates, NRE).

It is preferable according to the invention for the detergents according to the invention to contain at least one compound of formula (T1-3) as the anionic surfactant of formula (T1)

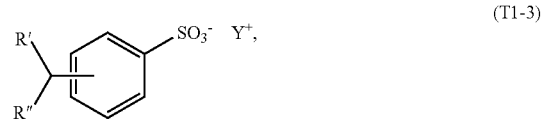 (T1-3)

in which
R' and R", independently, are H or alkyl, and together contain 9 to 19, preferably 9 to 15 and in particular 9 to 13 C atoms, and $Y^+$ indicates a monovalent cation or the n-th part of an n-valent cation (in particular $Na^+$) (proceeding from formula (T1): -A-=chemical bond, $R^1$=linear or branched alkyl aryl, $Y^+$=$Na^+$). A more particularly preferred representative can be described by the formula (T1-3a):

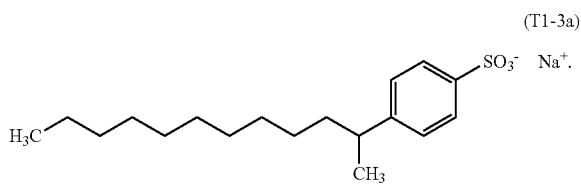 (T1-3a)

The detergents according to the invention preferably contain, as the surfactant of formula (T1), a combination of at least one fatty alcohol ether sulfate of formula (T1-1)

 (T1-1), in which
$R^1$ represents a linear or branched ($C_8$-$C_{18}$) alkyl group,
OZ represents an ethylene oxide (EO) grouping or a propylene oxide (PO) grouping,
n represents an integer from 1 to 50, preferably from 1 to 20 and in particular from 2 to 10, and
$Y^{*+}$ represents a monovalent cation or the n-th part of an n-valent cation,
and
at least one linear or branched alkylbenzene sulfonate of formula A-4

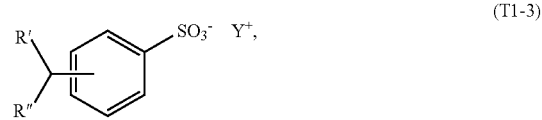 (T1-3)

in which R' and R" together contain 9 to 19, preferably 11 to 15 and in particular 11 to 13 C atoms and $Y^+$ represents a monovalent cation or the n-th part of an n-valent cation (in particular $Na^+$).

The liquid detergent can also contain soaps as an anionic surfactant. Saturated and unsaturated fatty acid soaps are suitable, such as the salts of lauric acid, myristic acid, palmitic acid, stearic acid, (hydrogenated) erucic acid and behenic acid, and in particular soap mixtures derived from natural fatty acids, such as coconut, palm kernel, olive oil or tallow fatty acids.

If the detergent according to the invention contains an anionic surfactant, it is in turn preferable for anionic surfactant to be contained in a total amount of from 4 to 70 wt. %, in particular from 10 to 50 wt. %, more preferably from 15 to 40 wt. %, based on the total weight of the detergent.

The detergent according to the invention can preferably contain at least one non-ionic surfactant as a surfactant. Preferred detergents thus contain at least one anionic surfactant and/or at least one non-ionic surfactant is contained. In a particularly preferable embodiment, the detergent according to the invention additionally contains at least one non-ionic surfactant in addition to an anionic surfactant. Suitable additional non-ionic surfactants include alkoxylated fatty acid alkyl esters, alkoxylated fatty acid amides, hydroxylated alkyl glycol ethers, polyhydroxy fatty acid amides, alkylphenol polyglycol ethers, amine oxides, alkyl (poly)glucosides and mixtures thereof.

Particularly preferably, the agent according to the invention contains at least one compound of formula (T2) as a non-ionic surfactant,

$$R^2-O-(XO)_m-H, \qquad (T2)$$

in which
$R^2$ represents a linear or branched $C_8$-$C_{18}$ alkyl group, an aryl group or an alkyl aryl group,
XO independently represents an ethylene oxide (EO) grouping or a propylene oxide (PO) grouping,
m represents integers from 1 to 50.

Particularly preferred groups $R^2$ of formula (T2) are derived from $C_{12}$-$C_{18}$ fatty alcohols, for example from coconut fatty alcohol, tallow fatty alcohol, lauryl, myristyl, cetyl or stearyl alcohol or from $C_8$-$C_{18}$ oxo alcohols.

According to formula (T2), XO preferably represents an ethylene oxide grouping.

According to formula (T2), the index m preferably represents a number from 1 to 20, and in particular from 2 to 10. Very particularly preferably, m represents the numbers 2, 3, 4, 5, 6, 7 or 8.

Non-ionic surfactants that are preferably used are alkoxylated, advantageously ethoxylated, in particular primary alcohols having preferably 8 to 18 C atoms and, on average, 4 to 12 mols of ethylene oxide (EO) per mol of alcohol, in which the alcohol group can be linear or preferably methyl-branched in the 2 position, or can contain linear and methyl-branched groups in admixture, as are usually present in oxo alcohol groups. However, alcohol ethoxylates having linear groups of alcohols of native origin having 12 to 18 C atoms, for example of coconut, palm, tallow fatty or oleyl alcohol, and an average of 4 to 8 EO per mole of alcohol are particularly preferred. Preferred ethoxylated alcohols include, for example, $C_{12}$-14 alcohols having 4 EO or 7 EO, $C_{9-11}$ alcohol having 7 EO, $C_{13-15}$ alcohols having 5 EO, 7 EO or 8 EO, $C_{12-18}$ alcohols having 5 EO or 7 EO, and mixtures thereof. Preferred alcohol ethoxylates have a narrowed homolog distribution (narrow range ethoxylates, NRE). In addition to or instead of these preferred non-ionic surfactants, fatty alcohols with more than 12 EO can also be used. Examples of these are tallow fatty alcohols with 14 EO, 25 EO, 30 EO, or 40 EO. Non-ionic surfactants that contain EO and PO groups together in the molecule can also be used according to the invention. Furthermore, a mixture of a (more highly) branched ethoxylated fatty alcohol and an unbranched ethoxylated fatty alcohol, such as a mixture of a $C_{16-18}$ fatty alcohol having 7 EO and 2-propylheptanol having 7 EO, is also suitable. Particularly preferably, the detergent according to the invention contains a $C_{12-18}$ fatty alcohol having 7 EO or a $C_{13-15}$ oxo alcohol having 7 EO as a non-ionic surfactant.

In principle, all the amine oxides found in the prior art for this purpose, i.e. compounds that have the formula $R^1R^2R^3NO$, in which each of $R^1$, $R^2$ and $R^3$, independently, is an optionally substituted $C_1$-$C_{30}$ hydrocarbon chain, can be used as the amine oxide. Amine oxides that are particularly preferably used are those in which $R^1$ is $C_{12}$-$C_{18}$ alkyl and $R^2$ and $R^3$ are, independently, each $C_1$-$C_4$ alkyl, in particular $C_{12}$-$C_{18}$ alkyl dimethyl amine oxides. Examples of representatives of suitable amine oxides are N-cocoalkyl-N,N-dimethyl amine oxide, N-tallow-alkyl-N,N-dihydroxyethyl amine oxide, myristyl-/cetyl dimethyl amine oxide or lauryl dimethyl amine oxide.

It is preferred according to the invention if the detergents according to the invention contain, based on their total weight, non-ionic surfactant in a total amount between 0 and 35 wt. % and preferably from 5 to 30 wt. %, very particularly preferably from 7 to 28 wt. %, in each case based on the total agent.

Preferred detergents of the present invention have a pH of from 6 to 11.5, preferably 6.5 to 9.5, more preferably 7.0 to 9.0 at 20° C.

The detergents according to the invention have in particular an excellent cleaning effect on bleachable soiling if they additionally contain at least one compound of formula (II) which is not complexed to a metal cation M of a transition metal or lanthanide of formula (I) (in particular not to a metal cation of the representative of M preferably mentioned under formula (I)). Preferred detergents are therefore characterized in that they additionally contain at least one free catechol compound of formula (II) or the salt thereof

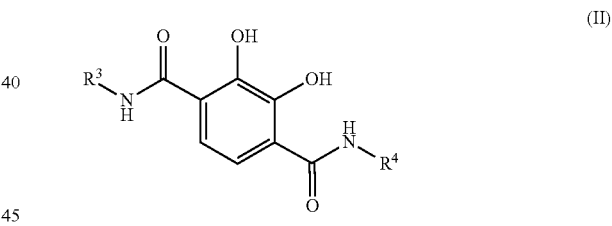

where
$R^3$ and $R^4$ independently represent a hydrocarbon group having 1 to 20 carbon atoms, which is optionally substituted by at least one group selected from hydroxy, $(C_1$-$C_4)$ alkoxy, $(C_1$-$C_4)$ alkoxy$(CH_2CH_2O)_n$—, —NR'R" or —N$^+$R'R"R'"X$^-$, where n=1 to 10, R', R" and R'" independently represent H or a linear or branched aliphatic hydrocarbon group having 1 to 3, preferably 1 to 2 carbon atoms and X$^-$ represents an anion, with the proviso that the catechol compound of formula (II) and the salt thereof are different from compounds of formula (I) (vide supra).

The "free catechol compound" of formula (II) is present in the context of the above proviso as an uncomplexed ligand and/or as a complex that is different from compounds of formula (I). The salt of the free catechol compound of formula (II) is present in deprotonated form on at least one of the OH groups which bind directly to the catechol phenyl ring, the resulting negative charge being neutralized by a corresponding cation equivalent. The salt of the free catechol compound can be dissociated in the detergent according to the invention and/or can be a complex to a cation equivalent as the central ion, said cation equivalent being different from the metal cation M of formula (I).

Preferred cation equivalents of the salt of the free catechol compound of formula (II) are selected from alkali metal ion (preferably Na$^+$ or K$^+$), alkaline earth metal ion (preferably Ca$^{2+}$ or Mg$^{2+}$) and alkanol ammonium ion. Preferred alkanol ammonium ions are 2-ammoninoethan-1-ol, tris(2-hydroxyethyl)ammonium, 3-ammoniopropan-1-ol, 4-ammoninbutan-1-ol, 5-amnoniopentan-1-ol, 1-ammoniopropan-2-ol, 1-ammoniobutan-2-ol, 1-ammoniopentan-2-ol, 1-ammoniopentan-3-ol, 1-ammoniopentan-4-ol, 3-ammonio-2-methylpropan-1-ol, 1-ammonio-2-methylpropan-2-ol, 3-ammoniopropan-1,2-diol, 2-ammonio-2-methylpropan-1,3-diol (especially 2-ammonioethan-1-ol, tris(2-hydroxyethyl)ammonium, 2-ammonio-2-methylpropan-1-ol, 2-ammonio-2-methyl-propan-1,3-diol), or mixtures thereof.

It is preferred in the detergent according to the invention that in formula (II) the groups R$^3$ and R$^4$ independently represent an alkyl group, an alkoxyalkyl group, a hydroxyalkyl group, a hydroxyalkyloxyalkyl group, (N-hydroxyethyl)-aminoethyl, (N-methoxyethyl)-aminoethyl or (N-ethoxyethyl)-aminoethyl, or an aromatic group (preferably methyl, ethyl, n-propyl, isopropyl, n-butyl, sec-butyl, tert-butyl, iso-butyl, n-pentyl, iso-pentyl, neopentyl, hexyl, 2-hydroxyethyl, 2-hydroxypropyl, 3-hydroxypropyl, (N-hydroxyethyl)-aminoethyl, (N-methoxyethyl)-aminoethyl or (N-ethoxyethyl)-aminoethyl or phenyl).

Preferred compounds of formula (II) are those in which the groups R$^3$ and R$^4$ are the same.

The preferred groups R$^3$ and R$^4$ of formula (II) are selected from the preferred groups R$^1$ and R$^2$ of formula (I).

The groups R$^3$ and R$^4$ of formula (II) are very particularly preferably selected depending on the groups R$^1$ and R$^2$ of formula (I), the groups R$^1$, R$^2$, R$^3$ and R$^4$ most preferably being identical.

It is particularly preferred if the detergent according to the invention contains the free catechol compound of formula (II) in a total amount of from 0.01 to 10.0 wt. % preferably from 0.1 to 5.0 wt. %.

The detergent according to the invention preferably contains water as a further constituent. Particularly preferred liquid detergents contain water in a total amount, based on the weight thereof, of from 5 to 90 wt. %, preferably 10 to 85 wt. %, particularly preferably 25 to 75 wt. %, and in particular 35 to 65 wt. %. Alternatively, the detergents can be low-water detergents, the total amount of water in a preferred embodiment being between 0 and 25 wt. %, in particular between 1 and 20 wt. % and particularly preferably between 2 and 18 wt. %, in each case based on the total detergent.

The water content as defined herein relates to the water content determined by means of Karl Fischer titration (Angewandte Chemie 1935, 48, 394-396; ISBN 3-540-12846-8 Eugen Scholz).

The detergent according to the invention is preferably transparent or translucent. If a detergent according to the invention has a residual light output (transmission) of at least 20% in the spectral range between 380 nm and 780 nm, based on the reference measurement, it is considered transparent within the meaning of the invention.

The transparency of the detergent according to the invention can be determined using various methods. The Nephelometric Turbidity Unit (NTU) is frequently used as an indication of transparency. It is a unit, used e.g. in water treatment, for measuring turbidity e.g. in liquids. It is a unit of turbidity measured using a calibrated nephelometer. High NTU values are measured for clouded detergents, whereas low values are determined for clear, transparent detergents.

The HACH Turbidimeter 2100Q from Hach Company, Loveland, Colo. (USA) is used with the calibration substances StablCal Solution HACH (20 NTU), StablCal Solution HACH (100 NTU) and StablCal Solution HACH (800 NTU), all of which can also be ordered from Hach Company. The measurement is filled with the composition to be analyzed in a 10 ml measuring cuvette having a cap and is carried out at 20° C.

At an NTU value (at 20° C.) of 60 or more, detergents have a perceptible turbidity within the meaning of the invention, as can be seen with the naked eye. It is therefore preferred if the detergents according to the invention have an NTU value (at 20° C.) of at most 120, more preferably at most 110, more preferably at most 100, particularly preferably of at most 80.

In the context of the present invention, the transparency of the detergents according to the invention was determined by a transmission measurement in the visual light spectrum over a wavelength range of from 380 nm to 780 nm at 20° C. For this purpose, a reference sample (water, fully desalinated) is first measured in a photometer (Specord S 600 from AnalytikJena) with a cuvette (layer thickness 10 mm) that is transparent in the spectrum to be examined. The cuvette is then filled with a sample of the detergent according to the invention and measured again. The sample is poured in in the liquid state and, if necessary, solidified in the cuvette and then measured.

It is preferred if the transparent detergent according to the invention has a transmission (20° C.) of preferably at least 25%, more preferably at least 30%, more preferably at least 40%, in particular at least 50%, particularly preferably at least 60%.

It is very particularly preferred if the transparent detergent according to the invention has a transmission (at 20° C.) of at least 30% (in particular of at least 40%, more preferably of at least 50%, particularly preferably of at least 60%) and an NTU value (at 20° C.) of at most 120 (more preferably at most 110, more preferably at most 100, particularly preferably at most 80).

In the context of a preferred embodiment according to the invention, the detergent according to the invention is liquid, has a yield point and additionally contains suspended solid particles (hereinafter also referred to as particles). Suspended solid particles of this type are understood to be solid substances that do not dissolve in the continuous phase of the detergent according to the invention at 20° C. and are present as a separate phase.

The particles are preferably selected from polymers, pearlescing pigments, microcapsules, speckles, or mixtures thereof.

Within the meaning of the present invention, microcapsules include any type of capsule known to a person skilled in the art, but in particular core-shell capsules and matrix capsules. Matrix capsules are porous shaped bodies that have a structure similar to a sponge. Core-shell capsules are shaped bodies that have a core and a shell. Capsules that have an average diameter X$_{50.3}$ (volume average) of from 0.1 to 200 µm, preferably from 1 to 100 µm, more preferably from 5 to 80 µm, particularly preferably from 10 to 50 µm and in particular from 15 to 40 µm are suitable as microcapsules. The average particle size diameter X$_{50.3}$ is determined by sieving or by means of a Camsizer particle size analyzer from Retsch.

The microcapsules of the invention preferably contain at least one active ingredient, preferably at least one odorant. These preferred microcapsules are perfume microcapsules.

In a preferred embodiment of the invention, the microcapsules have a semi-permeable capsule wall (shell).

A semi-permeable capsule wall within the meaning of the present invention is a capsule wall that is semi-permeable, i.e. continuously releases small amounts of the capsule core over time, without the capsules being destroyed or opened e.g. by tearing. These capsules continuously release small amounts of the active ingredient contained in the capsule, e.g. perfume, over a long period of time.

In another preferred embodiment of the invention, the microcapsules have an impermeable shell. An impermeable shell within the meaning of the present invention is a capsule wall that is substantially not permeable, i.e. releases the capsule core only by the capsule being damaged or opened. These capsules contain significant amounts of the at least one odorant in the capsule core, and therefore when the capsule is damaged or opened, a very intense fragrance is provided. The fragrance intensities thus achieved are generally so high that lower amounts of the microcapsules can be used in order to achieve the same fragrance intensity as for conventional microcapsules.

In a preferred embodiment of the invention, the detergent according to the invention contains both microcapsules having a semipermeable shell and microcapsules having an impermeable shell. By using both types of capsule, a significantly improved fragrance intensity can be provided over the entire laundry cycle.

In another preferred embodiment of the invention, the detergent according to the invention may also contain two or more different microcapsule types having semipermeable or impermeable shells.

High-molecular compounds are usually considered as materials for the shell of the microcapsules, such as protein compounds, for example gelatin, albumin, casein and others, cellulose derivatives, for example methylcellulose, ethylcellulose, cellulose acetate, cellulose nitrate, carboxymethylcellulose and others, and especially also synthetic polymers such as polyamides, polyethylene glycols, polyurethanes, epoxy resins and others. Preferably, melamine formaldehyde polymer, melamine urea polymer, melamine urea formaldehyde polymer, polyacrylate polymer or polyacrylate copolymer are used as the wall material, i.e. as the shell. Capsules according to the invention are for example, but not exclusively, described in US 2003/0125222 A1, DE 10 2008 051 799 A1 or WO 01/49817.

Preferred melamine formaldehyde microcapsules are prepared by melamine formaldehyde precondensates and/or the $C_1$-$C_4$ alkyl ethers thereof in water, by the at least one odor modulator compound and optionally other ingredients, such as at least one odorant, being condensed in the presence of a protective colloid. Suitable protective colloids are e.g. cellulose derivatives, such as hydroxyethyl cellulose, carboxymethyl cellulose and methylcellulose, polyvinylpyrrolidone, copolymers of N-vinylpyrrolidone, polyvinyl alcohols, partially hydrolyzed polyvinyl acetates, gelatin, arabic gum, xanthan gum, alginates, pectins, degraded starches, casein, polyacrylic acid, polymethacrylic acid, copolymerisates of acrylic acid and methacrylic acid, sulfonic acid group-containing water-soluble polymers having a content of sulfoethyl acrylate, sulfoethyl methacrylate or sulfopropyl methacrylate, and polymerisates of N-(sulfoethyl)-maleinimide, 2-acrylamido-2-alkyl sulfonic acids, styrene sulfonic acids and formaldehyde and condensates of phenol sulfonic acids and formaldehyde.

It is preferable for the surface of the microcapsules used according to the invention to be coated entirely or in part with at least one cationic polymer. Accordingly, at least one cationic polymer from polyquaternium-1, polyquaternium-2, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-22, polyquaternium-24, polyquaternium-27, polyquaternium-28, polyquaternium-29, polyquaternium-30, polyquaternium-31, polyquaternium-32, polyquaternium-33, polyquaternium-34, polyquaternium-35, polyquaternium-36, polyquaternium-37, polyquaternium-39, polyquaternium-43, polyquaternium-44, polyquaternium-45, polyquaternium-46, polyquaternium-47, polyquaternium-48, polyquaternium-49, polyquaternium-50, polyquaternium-51, polyquaternium-56, polyquaternium-57, polyquaternium-61, polyquaternium-69 or polyquaternium-86 is suitable as a cationic polymer for coating the microcapsules. Polyquaternium-7 is very particularly preferred. The polyquaternium nomenclature used in this application for the cationic polymers is taken from the declaration for cationic polymers according to the International Nomenclature of Cosmetic Ingredients (INCI declaration) for cosmetic raw materials.

Microcapsules that can preferably be used have an average diameter $X_{50.3}$ in the range of from 1 to 100 preferably from 5 to 95 in particular from 10 to 90 for example from 10 to 80 μm.

The shell of the microcapsules surrounding the core or (filled) cavity preferably has an average thickness in the range of from approximately 5 to 500 nm, preferably of from approximately 50 nm to 200 nm, in particular of from approximately 70 nm to approximately 180 nm.

Pearlescing pigments are pigments that have a pearlescent shine. Pearlescing pigments consist of thin sheets that have a high refraction index, and partially reflect the light and are partially transparent to the light. The pearlescent shine is generated by interference of the light hitting the pigment (interference pigment). Pearlescing pigments are usually thin sheets of the above-mentioned material, or contain the above-mentioned material as thin, multilayered films or as components arranged in parallel in a suitable carrier material.

The pearlescing pigments that can be used according to the invention are either natural pearlescing pigments such as fish silver (guanine/hypoxanthine mixed crystals from fish scales) or mother of pearl (from ground seashells), monocrystalline, sheet-like pearlescing pigments such as bismuth oxychloride and pearlescing pigments with a mica base and a mica/metal oxide base. The latter pearlescing pigments are mica that has been provided with a metal oxide coating.

By using the pearlescing pigments in the suspension according to the invention, shine and optionally also color effects are achieved.

Pearlescing pigments with a mica base and mica/metal oxide base are preferred according to the invention. Mica is a phyllosilicate. The most important representatives of these silicates are muscovite, phlogopite, paragonite, biotite, lepidolite, and margarite. In order to produce the pearlescing pigments in conjunction with metal oxides, mica, primarily muscovite or phlogopite, is coated with a metal oxide. Suitable metal oxides are, inter alia, $TiO_2$, $Cr_2O_3$, and $Fe_2O_3$. Interference pigments and colored luster pigments are obtained as pearlescing pigments according to the invention by suitable coating. These pearlescing pigment types additionally have color effects in addition to a glittering optical effect. Furthermore, the pearlescing pigments that can be used according to the invention also contain a color pigment which is not derived from a metal oxide.

The grain size of the pearlescing pigments that are preferably used is preferably between 1.0 μm and 100 μm, particularly preferably between 10.0 and 60.0 μm, at an average diameter $X_{50.3}$ (volume average).

Within the meaning of the invention, speckles are understood to mean macroparticles, in particular macrocapsules, that have an average diameter $X_{50.3}$ (volume average) of more than 300 μm, in particular from 300 to 1,500 μm, preferably from 400 to 1,000 μm.

Speckles are preferably matrix capsules. The matrix is preferably colored. The matrix is formed for example by gelation, polyanion-polycation interactions or polyelectrolyte-metal ion interactions, and this is well known in the prior art, just like the preparation of particles using these matrix-forming materials. An example of a matrix-forming material is alginate. In order to prepare alginate-based speckles, an aqueous alginate solution, optionally also containing the active ingredient or active ingredients to be included, is subject to dripping and is then hardened in a precipitation bath containing $Ca^{2+}$ ions or $Al^{3+}$ ions. Alternatively, other matrix-forming materials may be used instead of alginate.

The detergents according to the invention preferably additionally contain at least one further active substance. Active substances within the meaning of the present invention are in particular:

textile care agents such as plasticizers, water and re-soiling repellents and impregnating agents, bleach activators, enzymes, silicone oils, anti-redeposition agents, optical brighteners, graying inhibitors, anti-shrink agents, anti-crease agents, dye transfer inhibitors, anti-microbial active ingredients, germicides, fungicides, antioxidants, antistatic agents, ironing aids, anti-swelling and anti-slip agents, UV absorbers, cationic polymers, skin care products or perfume (oil) or fragrances.

The detergent according to the invention is preferably substantially free of additional dyes.

At least one active substance is preferably selected from enzymes, optical brighteners, builders, solvents, anti-redeposition agents, color transfer inhibitors, preservatives, perfume or mixtures of at least two of the aforementioned active substances.

The detergent may also contain an additional bleaching agent different from the catechol compound according to formula (II). In a preferred embodiment, substantially no further bleaching agent is contained.

It is preferred if the detergent according to the invention additionally contains at least one enzyme, in particular selected from protease, amylase, lipase, mannanase, cellulase, pectate lyase or mixtures thereof.

At the protein level, "variant" is the term corresponding to "mutant" at the nucleic acid level. The precursor or starting molecules can be wild-type enzymes, i.e. those which can be obtained from natural sources. They can also be enzymes which are variants in themselves, i.e. which have already been modified compared to the wild-type molecules. These include, for example, point mutants, those with changes in the amino acid sequence, over several positions or longer contiguous regions, or else hybrid molecules which are composed of complementary portions of different wild-type enzymes.

Amino acid exchanges are understood to mean substitutions of one amino acid for another amino acid. According to the invention, such substitutions are specified in the internationally used single-letter code, indicating the positions in which the exchange takes place, optionally combined with the relevant amino acids. "Exchange in position 320" means, for example, that a variant in the position that has position 320 in the sequence of a reference protein has a different amino acid. Such exchanges are usually carried out at the DNA level via mutations of individual base pairs (see above). "R320K" means, for example, that the reference enzyme at position 320 has the amino acid arginine, while the variant under consideration has the amino acid lysine at the position that can be homologated therewith. "320K" means that any, i.e. usually a naturally prescribed, amino acid at a position which corresponds to position 320 is replaced by a lysine which is located precisely at this point in the present molecule. "R320K, L" means that the amino acid arginine in position 320 is replaced by lysine or leucine. And "R320X" means that the amino acid arginine in position 320 is replaced by any other amino acid.

In principle, the amino acid exchanges according to the invention designated by the present application are not limited to being the only exchanges in which the variant in question differs from the wild-type molecule. It is known in the art that the advantageous properties of individual point mutations can complement one another. Thus, embodiments of the present invention include all variants which, in addition to other exchanges with the wild-type molecule, also have the exchanges according to the invention.

Furthermore, in principle it does not matter in what order the amino acid exchanges in question have been carried out, i.e. whether a corresponding point mutant is developed according to the invention or first a variant according to the invention is generated from a wild-type molecule and is developed in accordance with other teachings to be found in the prior art. Several exchanges can also be carried out simultaneously in a mutagenesis approach, for example those according to the invention and others together.

It is preferred according to the invention if at least one protease is contained as the enzyme. A protease is an enzyme that cleaves peptide bonds by means of hydrolysis. According to the invention, each of the enzymes from class E.C. 3.4 is included (including each of the thirteen subclasses). The EC number corresponds to the Enzyme Nomenclature 1992 of the NC-IUBMB, Academic Press, San Diego, Calif., including supplements 1 to 5, published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650.

Subtilase designates a subset of the serine proteases. The serine proteases or serine peptidases are a subset of the proteases that have serine in the active center of the enzyme that forms a covalent adduct with the substrate. Furthermore, the subtilases (and the serine proteases) are characterized in that they have two further amino acid residues in the active center in addition to said serine with histidine and aspartame. The subtilases can be divided into 6 subclasses, namely the subtilisin family, the thermitase family, the proteinase K family, the lantibiotic peptidase family, the kexin family and the pyrrolysine family. The proteases which are preferably excluded or preferably contained in reduced amounts as part of the detergents according to the invention are endopeptidases (EC 3.4.21).

According to the invention, "protease activity" is present if the enzyme has proteolytic activity (EC 3.4). Different types of protease activity are known: The three main types are:

trypsin-like, with cleavage of the amide substrate after the amino acids Arg or Lys at P1;
chymotrypsin-like, with cleavage after one of the hydrophobic amino acids at P1; and
elastase-like, with cleavage of the amide substrate after Ala at P1.

The protease activity can be determined by the method described in *Tenside*, Volume 7 (1970), pp. 125-132. Accordingly, it is given in PE (protease units). The protease activity of an enzyme can be determined according to standard methods, such as in particular using BSA as substrate (bovine albumin) and/or using the AAPF method.

Surprisingly, it was found that a protease of the alkaline protease type from *Bacillus lentus* DSM 5483 or a protease sufficiently similar thereto (based on the sequence identity), which has several of these changes in combination, is particularly suitable for use in the detergent according to the invention and is advantageously stabilized therein in an improved manner. Advantages of using this protease thus arise in particular with regard to washing performance and/or stability.

The identity of nucleic acid or amino acid sequences is determined by a sequence comparison. This sequence comparison is based on the BLAST algorithm established and commonly used in the prior art (cf. for example Altschul, S. F., Gish, W., Miller, W., Myers, E. W. & Lipman, D. J. (1990) "Basic local alignment search tool." J. Mol. Biol. 215: 403-410, and Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs"; Nucleic Acids Res., 25, S.3389-3402) and takes place in principle by similar sequences of nucleotides or amino acids in the nucleic acid or amino acid sequences being assigned to one another. The assignment of the relevant positions shown in a table is referred to as an alignment. Another algorithm available in the prior art is the FASTA algorithm. Sequence comparisons (alignments), in particular multiple sequence comparisons, are created using computer programs. The Clustal series (cf. for example Chenna et al. (2003): Multiple sequence alignment with the Clustal series of programs. Nucleic Acid Research 31, 3497-3500), T-Coffee (cf. for example Notredame et al. (2000): T-Coffee: A novel method for multiple sequence alignments. J. Mol. Biol. 302, 205-217) or programs based on these programs or algorithms are often used, for example. In the present invention, all sequence comparisons (alignments) were created using the computer program Vector NTI® Suite 10.3 (Invitrogen Corporation, 1600 Faraday Avenue, Carlsbad, Calif., USA) with the specified standard parameters, the AlignX module of which program for the sequence comparisons is based on ClustalW.

Such a comparison also allows conclusions to be drawn regarding the similarity of the compared sequences. It is usually given in percent identity, i.e. the proportion of identical nucleotides or amino acid residues in said sequences or in an alignment of corresponding positions. The broader concept of homology takes conserved amino acid exchanges into account in the case of amino acid sequences, i.e. amino acids having similar chemical activity, since they usually perform similar chemical activities within the protein. Therefore, the similarity between the compared sequences can also be expressed in percent homology or percent similarity. Identity and/or homology information can be provided regarding whole polypeptides or genes or only regarding individual regions. Homologous or identical regions of different nucleic acid or amino acid sequences are therefore defined by matches in the sequences. Such regions often have identical functions. They can be small and comprise only a few nucleotides or amino acids. Often, such small regions perform essential functions for the overall activity of the protein. It may therefore be expedient to relate sequence matches only to individual, optionally small regions. Unless stated otherwise, however, identity or homology information in the present application relates to the entire length of the particular nucleic acid or amino acid sequence indicated.

The concentration of the protease in the detergent is from 0.001 to 0.1 wt. %, preferably from 0.01 to 0.06 wt. %, based on active protein.

The detergents according to the invention (particularly preferably in addition to the protease) preferably contain at least one enzyme selected from α-amylase, cellulase, mannanase, lipase, pectate lyase as an enzyme.

In general, the enzymes contained in a detergent according to the invention can be adsorbed on carrier substances and/or embedded in coating substances to protect the enzymes from premature inactivation.

The enzymes obtained can be added to the detergents according to the invention in any form established according to the prior art. These include in particular the solid preparations obtained by granulation, extrusion or lyophilization, advantageously as concentrated as possible, low in water and/or mixed with stabilizers. In an alternative form of administration, the enzymes can also be encapsulated, for example by spray-drying or extruding the enzyme solution together with a preferably natural polymer or in the form of capsules, for example those in which the enzymes are enclosed in a solidified gel, or in the form of the core-shell type in which an enzyme-containing core is coated with a water-, air-, and/or chemical-impermeable protective layer. Further active ingredients such as stabilizers, emulsifiers, pigments or dyes can additionally be applied in overlaid layers. Such capsules are applied using methods which are known per se, for example by shaking or rolling granulation or in fluidized bed processes. Advantageously, such granules are low in dust, for example due to the application of polymeric film-formers, and stable in storage due to the coating.

The detergents preferably additionally contain at least one cellulase. A cellulase is an enzyme. Synonymous terms can be used for cellulases, in particular endoglucanase, endo-1, 4-beta-glucanase, carboxymethyl cellulose, endo-1,4-beta-D-glucanase, beta-1,4-glucanase, beta-1,4-endoglucan hydrolase, cellulose extrinase or avicelase. Within the meaning of the invention, whether or not an enzyme is a cellulase is decided by its ability to hydrolyze 1,4-β-D-glycosidic bonds in cellulose.

Cellulases (endoglucanases, EG) that can be formulated according to the invention include, for example, the fungal cellulase preparation that is rich in endoglucanase (EG) and the developments thereof, which are provided by Novozymes under the trade name Celluzyme®. The products Endolase® and Carezyme® also available from Novozymes are based on 50 kD-EG and 43 kD-EG, respectively, from *Humicola insolens* DSM 1800. Other commercial products from this company that can be used are Cellusoft®, Renozyme®, and Celluclean®. It is also possible to use cellulases, for example, which are available from AB Enzymes, Finland, under the trade names Ecostone® and Biotouch®, and which are based on 20 kD-EG from *Melanocarpus* at least in part. Other cellulases from AB Enzymes are Econase® and Ecopulp®. Other suitable cellulases are from *Bacillus* sp. CBS 670.93 and CBS 669.93, the cellulase from *Bacillus* sp. CBS 670.93 being available from Danisco/Genencor under the trade name Puradax®. Other commercial products that can be used from Danisco/Genencor are "Genencor detergent cellulase L" and IndiAge®Neutra.

Variants of these enzymes that can be obtained by point mutations can also be used according to the invention. Particularly preferred cellulases are *Thielavia terrestris* cellulase variants which are disclosed in the international laid-open application WO 98/12307, cellulases from *Melanocarpus*, in particular *Melanocarpus albomyces*, which are disclosed in the international laid-open application WO 97/14804, cellulases of the EGIII type from *Trichoderma reesei* which are disclosed in the European patent application EP 1 305 432 or variants obtainable therefrom, in particular those which are disclosed in the European patent applications EP 1240525 and EP 1305432, and cellulases which are disclosed in the international laid-open applications WO 1992006165, WO 96/29397 and WO 02/099091. Reference is therefore expressly made to their respective disclosures, or the disclosure content thereof in this respect is therefore expressly included in the present invention.

Particularly preferred detergents according to the invention are characterized in that at least one cellulase 20K-cellulase that can be obtained from *Melanocarpus* sp. or *Myriococcum* sp. or those having a homology thereto of more than 80% (in order of increasing preference 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99.0%, 99.1%, 99.2%, 99.3%, 99.4%, 99.5%, 99.6%, 99.7%, 99.8% or 99.9%) as an additional cellulase.

The 20K-cellulase that can be obtained from *Melanocarpus* sp. or *Myriococcum* sp. is known from the international patent application WO 97/14804. As described therein, it has a molecular weight of approximately 20 kDa and exhibits at least 80% of its maximum activity at 50° C. in the pH range of from 4 to 9, with almost 50% of the maximum activity remaining at pH 10. As also described therein, it can be isolated from *Melanocarpus albomyces* and produced in genetically engineered *Trichoderma reseei* transformants. Cellulases having a homology of more than 80% (in order of increasing preference 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99.0%, 99.1%, 99.2%, 99.3%, 99.4%, 99.5%, 99.6%, 99.7%, 99.8% or 99.9%) to the 20K-cellulase can also be used within the meaning of the present invention.

K20-cellulase is preferably used in amounts such that a detergent according to the invention has a cellulolytic activity of from 1 NCU/g to 500 NCU/g (can be determined by the hydrolysis of 1 wt. % carboxymethyl cellulose at 50° C. and neutral pH and determination of the reducing sugars released in the process using dinitrosalicylic acid, as described by M. J. Bailey et al. in Enzyme Microb. Technol. 3 153 (1981); 1 NCU defines the amount of enzyme that produces reducing sugars in an amount that corresponds to 1 nmol glucose per second), in particular from 2 NCU/g to 400 NCU/g and particularly preferably from 6 NCU/g to 200 NCU/g. In addition, the detergent according to the invention can optionally contain further cellulases.

A detergent according to the invention preferably contains 0.001 mg to 0.5 mg, in particular 0.02 mg to 0.3 mg, of cellulolytic protein per gram of the total detergent. The protein concentration can be determined using known methods, for example the bicinchoninic acid method (BCA method, Pierce Chemical Co., Rockford, Ill.) or the Biuret method (A. G. Gornall, C. S. Bardawill and M. M. David, J. Biol. Chem. 177, 751-766, 1948).

According to the invention, it is in turn particularly preferred, in addition to at least one first cellulase 20K-cellulase that can be obtained from *Melanocarpus* sp. or *Myriococcum* sp. or those having a homology thereto of more than 80% (in order of increasing preference 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99.0%, 99.1%, 99.2%, 99.3%, 99.4%, 99.5%, 99.6%, 99.7%, 99.8% or 99.9%), to use at least one further, second cellulase that is different from the first cellulase.

It is preferred according to the invention if the detergents according to the invention additionally contain at least one lipase. Lipase enzymes preferred according to the invention are selected from at least one enzyme from the group which is formed from triacylglycerol lipase (E.C. 3.1.1.3) and lipoprotein lipase (E.C. 3.1.1.34) and monoglyceride lipase (E.C. 3.1.1.23).

Furthermore, the lipase preferably contained in a detergent according to the invention is naturally present in a microorganism of the species *Thermomyces lanuginosus* or *Rhizopus oryzae* or *Mucor javanicus* or is derived from the aforementioned naturally present lipases by mutagenesis. The detergents according to the invention particularly preferably contain at least one lipase which is naturally present in a microorganism of the *Thermomyces lanuginosus* type or is derived from the aforementioned lipases naturally present in *Thermomyces lanuginosus* by mutagenesis. In this context, naturally present means that the lipase is a separate enzyme of the microorganism. The lipase can thus be expressed in the microorganism by a nucleic acid sequence that is part of the chromosomal DNA of the microorganism in its wild-type form. It or the nucleic acid sequence coding for it is therefore present in the wild-type form of the microorganism and/or can be isolated from the wild-type form of the microorganism. In contrast, a lipase that is not naturally present in the microorganism or the nucleic acid sequence coding for it would have been introduced into the microorganism in a targeted manner using genetic engineering methods, such that the microorganism would have been enriched with the lipase or the nucleic acid sequence coding for it. However, a lipase which is naturally present in a microorganism of the species *Thermomyces lanuginosus* or *Rhizopus oryzae* or *Mucor javanicus* may well have been produced recombinantly by another organism.

The fungus *Thermomyces lanuginosus* (also known as *Humicola lanuginosa*) belongs to the class of Eurotiomycetes (subclass Eurotiomycetidae), here to the order of the Eurotiales and here to the family Trichocomaceae and the genus *Thermomyces*. The fungus *Rhizopus oryzae* belongs to the class of the Zygomycetes (subclass Incertae sedis), here to the order Mucorales and here again to the family Mucoraceae and the genus *Rhizopus*. The fungus *Mucor javanicus* also belongs to the class of the Zygomycetes (subclass Incertae sedis), here to the order Mucorales and again to the family Mucoraceae, and then to the genus *Mucor*. The names *Thermomyces lanuginosus*, *Rhizopus oryzae* and *Mucor javanicus* are the biological species names within the particular genus.

Preferred lipases according to the invention are the lipase enzymes available from Amano Pharmaceuticals under the names Lipase M-AP10®, Lipase LE® and Lipase F® (also Lipase JV®). For example, Lipase F® is naturally present in *Rhizopus oryzae*. Lipase M-AP10® is naturally present in *Mucor javanicus*, for example.

Detergents of a very particularly preferred embodiment of the invention contain at least one lipase which is selected from at least one or more polypeptides with an amino acid sequence which is at least 90% (and in order of increasing preference at least 81%, 82%, 83%, 84%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99.0%, 99.1%, 99.2%, 99.3%, 99.4%, 99.5%, 99.6%, 99.7%, 99.8%, 99.9%) identical to the wild-type lipase from the strain DSM 4109 *Thermomyces lanuginosus*. It is again preferred if, proceeding from said wild-type lipase from the strain DSM 4109, there is at least the amino acid change N233R.

Within the scope of a further embodiment, in particular those lipases derived from the wild-type lipase from the strain DSM 4109 which are selected from at least one lipase enzyme according to WO 00/60063 A1 are preferably used according to the invention. Reference is expressly made in full to the disclosure in WO 00/60063 A1.

It is particularly preferred to use at least one lipase in the detergents according the invention which is derived from the wild-type lipase from the strain DSM 4109 and in which, proceeding from said wild-type lipase, at least one substitution of an electrically neutral or negatively charged amino acid by a positively charged amino acid was carried out. The charge is determined in water at pH 10. Negative amino acids within the meaning of the invention are E, D, Y and C. Positively charged amino acids within the meaning of the invention are R, K and H, in particular R and K. Neutral amino acids within the meaning of the invention are G, A, V, L, I, P, F, W, S, T, M, N, Q and C if C forms a disulfide bridge.

In the context of this embodiment of the invention, it is also preferred if, proceeding from the wild-type lipase from the strain DSM 4109, at least one of the following amino acid exchanges is present in positions D96L, T213R and/or N233R, particularly preferably T213R and N233R.

A highly preferred lipase is commercially available from Novozymes (Denmark) under the trade name Lipex® and can advantageously be used in the detergents according to the invention. The lipase Lipex® 100 L (ex Novozymes A/S, Denmark) is particularly preferred. Preferred detergents are characterized in that, based on the total weight of the detergent, said lipase enzyme from Lipex® 100 L is contained in a total amount of from 0.01 to 1.0 wt. %, in particular 0.02 to 0.1 wt. %.

The detergents according to the invention can additionally contain at least one mannanase as the enzyme. A mannanase contained in the detergent according to the invention catalyzes the hydrolysis of 1,4-beta-D-mannosidic bonds in mannans, galactomannans, glucomannans and galactoglucomannans within the scope of its mannanase activity. Said mannanase enzymes according to the invention are classified according to the Enzyme Nomenclature as E.C. 3.2.1.78.

The mannanase activity of a polypeptide or enzyme can be determined according to test methods known in the literature. For example, a test solution is placed in holes with a diameter of 4 mm in an agar plate containing 0.2 wt. % of AZGL galactomannan (carob), i.e. substrate for the endo-1,4-beta-D-mannanase essay, available under catalog number I-AZGMA from Megazyme (http://www.megazyme.com).

Suitable detergents according to the invention contain, for example, the mannanase which is marketed by Novozymes under the name Mannaway®.

Mannanase enzymes have been identified in numerous *Bacillus* organisms:

WO 99/64619 discloses examples of liquid, protease-containing detergents having a high total surfactant content of at least 20 wt. %, which additionally comprise mannanase enzyme.

The detergents according to the invention preferably contain mannanase in a total amount of from 0.01 to 1.0 wt. %, in particular 0.02 to 0.1 wt. %, based on the total weight of the detergent.

Mannanase polypeptides from strains of the *Thermoanaerobacter* group, such as *Caldicellulosiruptor*, are preferably suitable according to the invention. Mannanase polypeptides of the fungi *Humicola* or *Scytalidium*, in particular of the species *Humicola insolens* or *Scytalidium thermophilum*, can also be used in the context of the invention.

It is particularly preferred according to the invention if the detergents according to the invention, as a mannanase enzyme, at least one mannanase polypeptide from gram-positive alkalophilic strains of *Bacillus*, in particular selected from at least one representative of the group of *Bacillus subtilis, Bacillus lentus, Bacillus clausii, Bacillus agaradhaerens, Bacillus brevis, Bacillus stearothermophilus, Bacillus alkalophilus, Bacillus amyloliquefaciens, Bacillus coagulans, Bacillus circulans, Bacillus lautus, Bacillus thuringiensis, Bacillus cheniformis*, and *Bacillus* sp., particularly preferably selected from at least one representative of the group of *Bacillus* sp. 1633, *Bacillus* sp. AAI 12, *Bacillus clausii, Bacillus agaradhaerens* and *Bacillus licheniformis*.

A preferred mannanase according to the invention is selected from at least one representative from the group that is formed from
i) polypeptides which comprise an amino acid sequence of which the sequence is at least 90% (in order of increasing preference at least 90.5%, 91%, 91.5%, 92%, 92.5%, 93%, 93.5%, 94%, 94.5%, 95%, 95.5%, 96%, 96.5%, 97%, 97.5%, 98%, 98.5%, 99.0%, 99.1%, 99.2%, 99.3%, 99.4%, 99.5%, 99.6%, 99.7% or 99.8%) identical to the polypeptide according to SEQ ID NO:1 (cf. sequence protocol from WO 99/64619), and
ii) polypeptides which are a fragment of (i).

It is in turn preferred if said preferred mannanase is contained in the detergent according to the invention in a total amount of from 0.01 to 1.0 wt. %, in particular 0.02 to 0.1 wt. %, in each case based on the total weight of the detergent.

The detergent according to the invention particularly preferably contains, in addition to the preferred protease of the alkaline protease type from *Bacillus lentus* DSM 5483 or in addition to the protease which is sufficiently similar thereto (based on the sequence identity) and which has several of these changes in combination, additionally at least one α-amylase.

α-amylases (E.C 3.2.1.1) hydrolyze, as an enzyme, internal α-1,4-glycosidic bonds of starch and starch-like polymers. This α-amylase activity is measured, for example, according to the applications WO 97/03160 A1 and GB 1296839 in KNU (Kilo Novo units). 1 KNU represents the amount of enzyme that hydrolyzes 5.25 g of starch (available from Merck, Darmstadt, Germany) per hour at 37° C., pH 5.6 and in the presence of 0.0043 M calcium ions. An alternative activity determination method is the so-called DNS method, which is described for example in WO 02/10356 A2. The oligosaccharides, disaccharides and glucose units released by the enzyme during the hydrolysis of starch are then detected by oxidation of the reducing ends with dinitrosalicylic acid (DNS). The activity is obtained in µmol reducing sugars (based on maltose) per min and ml; this results in activity values in TAU. The same enzyme can be determined using different methods, although the respective conversion factors can vary depending on the enzyme and must therefore be determined using a standard. It can roughly be calculated that 1 KNU corresponds to approx. 50 TAU. Another activity determination method is the measurement using the Quick-Start® test kit from Abbott, Abott Park, Ill., USA.

A preferred field of use of the detergents according to the invention is in the cleaning of textiles. Because detergents for textiles mostly have alkaline pH values, α-amylases which are active in the alkaline medium are used in particular for this purpose. These are produced and secreted by microorganisms, i.e. fungi or bacteria, especially those of the genera *Aspergillus* and *Bacillus*. Proceeding from these natural enzymes, there is still an almost unmanageable abundance of variants which have been derived via mutagenesis and which have specific advantages depending on the field of use.

Examples of this are the α-amylases from *Bacillus licheniformis*, from *B. amyloliquefaciens* and from *B. stearothermophilus* as well as the improved developments thereof for use in detergents. The enzyme from *B. licheniformis* is available from Novozymes under the name Termamyl® and from Genencor under the name Purastar®ST. Development products of this α-amylase are available from Novozymes under the trade names Duramyl® and Termamyl®ultra, from Genencor under the name Purastar®OxAm, and from Daiwa Seiko Inc., Tokyo, Japan, as Keistase®. The α-amylase from *B. amyloliquefaciens* is marketed by Novozymes under the name BAN®, and derived variants from the α-amylase from *B. stearothermophilus* are marketed under the names BSG® and Novamyl®, also by Novozymes.

Examples of α-amylases from other organisms are the developments of the α-amylase from *Aspergillus niger* and *A. oryzae* available under the trade name Fungamyl® from Novozymes. Another commercial product is, for example, the Amylase-LT®.

The prior art includes, inter alia, the three patent applications WO 96/23873 A1, WO 00/60060 A2 and WO 01/66712 A2 which have been registered by Novozymes. WO 96/23873 A1 describes, in part, several different point mutations in a total of more than 30 different positions in four different wild-type amylases and claims them for all amylases which are at least 80% identical to one of these four; they are said to have altered enzymatic properties with regard to thermal stability, oxidation stability and calcium dependence. WO 00/60060 A2 also names a large number of possible amino acid exchanges in 10 different positions on the α-amylases from two different microorganisms and claims them for all amylases with a homology of at least 96% identity thereto. Finally, WO 01/66712 A2 designates 31 different amino acid positions, some of which are identical to those mentioned above, which have been mutated in one of the two α-amylases mentioned in WO 00/60060 A2.

WO 96/23873 A1, for example, specifically provides the possibility of replacing an M in position 9 in said α-amylases according to the AA560 count with an L, of replacing M with L in position 202 and of deleting the amino acids located in positions 182 and 183 (or 183 and 184). WO 00/60060 A2 specifically discloses, inter alia, the amino acid variation N195X (i.e. in principle with respect to any other amino acid). WO 01/66712 A2 discloses, inter alia, the amino acid variations R118K, G186X (including in particular the G186R exchange, which is not relevant here), N299X (including in particular the N299A exchange, which is not relevant here), R320K, E345R and R458K.

The detergent according to the invention very particularly preferably contains, in addition to the preferred protease of the alkaline protease type from *Bacillus lentus* DSM 5483 or a protease which is sufficiently similar thereto (based on the sequence identity) and which has several of these changes in combination, additionally at least one α-amylase which, at temperatures between 10 and 20° C. has a higher activity than the amylase having the trade name "Stainzyme 12 L" from Novozymes.

Detergents that are preferred according to the invention contain α-amylase in a total amount of from 0.01 to 1.0 wt. %, in particular 0.02 to 1 wt. %.

At least one optical brightener is preferably selected from the substance classes of dis-tyrylbiphenyls, stilbenes, 4,4"-diamino-2,2"-stilbene disulfonic acids, cumarines, dihydroquinolones, 1,3-diarylpyrazolines, naphthalic acid imides, benzoxazole systems, benzisoxazole systems, benzimidazole systems, pyrene derivatives substituted with heterocycles, and mixtures thereof. These substance classes of optical brighteners have a high stability, a high light and oxygen resistance and a high affinity for fibers.

The following optical brighteners, which are selected from the group consisting of disodium-4,4'-bis-(2-morpholino-4-anilino-s-triazin-6-ylamino)stilbene disulfonate, disodium-2,2'-bis-(phenyl-styryl)disulfonate, 4,4'-bis[(4-anilino-6-[bis(2-hydroxyethyl)amino]-1,3,5-triazin-2-yl)amino]stilbene-2,2'-disulfonic acid, hexasodium-2,2'-[vinylenebis[(3-sulphonato-4,1-phenylene)imino[6-(diethylamino)-1,3,5-triazin-4,2-diyl]imino]]bis-(benzene-1,4-disulfonate), 2,2'-(2,5-thiophenediyl)bis[5-1,1-dimethylethyl)-benzoxazol (e.g. available as Tinopal® SFP from BASF SE) and/or 2,5-bis(benzoxazol-2-yl)thiophene, can be incorporated in a particularly effective and stable manner.

According to the invention, the detergent can also comprise builders. Polymeric polycarboxylates are suitable as builders, for example. These are, for example, the alkali metal salts of polyacrylic acid or of polymethacrylic acid, for example those having a relative molecular mass of from 600 to 750,000 g/mol.

Suitable polymers are in particular polyacrylates which preferably have a molecular mass of from 1,000 to 15,000 g/mol. Due to their superior solubility, the short-chain polyacrylates, which have molar masses of from 1,000 to 10,000 g/mol, and particularly preferably from 1,000 to 5,000 g/mol, can in turn be preferred from this group.

In addition, copolymeric polycarboxylates are suitable, in particular those of acrylic acid with methacrylic acid and of acrylic acid or methacrylic acid with maleic acid. To improve water solubility, the polymers can also contain allyl sulfonic acids, such as allyloxybenzene sulfonic acid and methallyl sulfonic acid, as monomers.

Suitable builders that can be contained in the detergent according to the invention are in particular also silicates, aluminum silicates (in particular zeolites), carbonates, salts of organic di- and polycarboxylic acids, and mixtures of these substances. Organic builders are particularly suitable as additional builders, for example the polycarboxylic acids which can be used in the form of the sodium salts thereof or as acids, with polycarboxylic acids being understood to mean those carboxylic acids that carry more than one acid function. These include, for example, adipic acid, succinic acid, glutaric acid, malic acid, tartaric acid, maleic acid, fumaric acid, saccharic acids, aminocarboxylic acids, in particular glutamic acid-N,N-diacetic acid (GLDA) and methylglycine-N,N-diacetic acid (MGDA), and mixtures thereof. Polymeric polycarboxylates are also suitable as builders. These are, for example, the alkali metal salts of polyacrylic acid or of polymethacrylic acid, for example those having a relative molecular mass of from 600 to 750,000 g/mol. Suitable polymers are in particular polyacrylates which preferably have a molecular mass of from 1,000 to 15,000 g/mol. Due to their superior solubility, the short-chain polyacrylates, which have molar masses of from 1,000 to 10,000 g/mol, and particularly preferably from 1,000 to 5,000 g/mol, can in turn be preferred from this group. In addition, copolymeric polycarboxylates are suitable, in particular those of acrylic acid with methacrylic acid and of acrylic acid or methacrylic acid with maleic acid. To improve water solubility, the polymers can also contain allyl sulfonic acids, such as allyloxybenzene sulfonic acid and methallyl sulfonic acid, as monomers. Soluble builders, such as acrylic polymers having a molar mass of from 1,000 to 5,000 g/mol, are preferably used in liquid components.

However, soluble builders, such as citric acid, or acrylic polymers having a molar mass of from 1,000 to 5,000 g/mol are particularly preferably used.

The detergent preferably also contains one or more non-aqueous solvents. Suitable non-aqueous solvents include mono- or polyhydric alcohols or glycol ethers, such as ethanol, n-propanol, i-propanol, butanols, glycol, propanediol, butanediol, methylpropanediol, glycerol, glycols, such as diglycol, propyl diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol mono methyl ether, dipropylene glycol mono ethyl ether, methoxytriglycol, ethoxytriglycol, butoxytriglycol, 1-butoxyethoxy-2-propanol, 3-methyl-3-methoxybutanol, 2,2-dimethyl-4-hydroxymethyl-1,3-dioxolane, propylene-glycol-t-butylether, di-n-octylether, and low-molecular polyalkylene glycols, such as PEG 400, and mixtures of these solvents.

Preferably, the solvents are selected from ethanol, n-propanol, i-propanol, butanols, glycol, propanediol, butanediol, methylpropanediol, glycerol, diglycol, propyl diglycol, butyl diglycol, hexylene glycol, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ether, propylene glycol ethyl ether, propylene glycol propyl ether, dipropylene glycol mono methyl ether, dipropylene glycol mono ethyl ether, methoxytriglycol, ethoxytriglycol, butoxytriglycol, 1-butoxyethoxy-2-propanol, 3-methyl-3-methoxybutanol, propylene-glycol-t-butylether, di-n-octylether, and mixtures of these solvents.

Furthermore, the detergents according to the invention can also contain compounds that positively influence the capability for washing out oil and grease from textiles, or what are referred to as soil-release active ingredients. This effect is particularly apparent when a textile is soiled which has been previously washed several times using an agent that contains this deoiling and degreasing component. Preferred deoiling and degreasing components include, for example, non-ionic cellulose ethers such as methylcellulose and methylhydroxypropylcellulose having a proportion of from 15 to 30 wt. % of methoxyl groups and from 1 to 15 wt. % of hydroxypropoxyl groups, in each case based on the non-ionic cellulose ether, and the polymers of phthalic acid and/or terephthalic acid known from the prior art, or derivatives thereof, with monomeric and/or polymeric diols, in particular polymers of ethylene terephthalates and/or polyethylene glycol terephthalates or anionically and/or non-ionically modified derivatives thereof. These are commercially available, for example, under the trade name Texcare®.

Antiredeposition agents can be used in particular on (co)polymers based on polyethyleneimine, polyvinyl acetate and polyethylene glycol, preferably in mixtures with antiredeposition agents.

The detergent can preferably also contain dye transfer inhibitors, preferably in amounts of from 0.1 wt. % to 2 wt. %, in particular from 0.1 wt. % to 1 wt. %, which, in a preferred embodiment of the invention, are polymers of vinylpyrrolidone, vinyl imidazole or vinyl pyridine-N-oxide or copolymers thereof.

The function of graying inhibitors is to keep the dirt that is removed from the textile fiber suspended in the liquor. Water-soluble colloids, which are usually organic, are suitable for this purpose, for example starch, sizing material, gelatin, salts of ethercarboxylic acids or ethersulfonic acids of starch or of cellulose, or salts of acidic sulfuric acid esters of cellulose or of starch. Water-soluble polyamides containing acid groups are also suitable for this purpose. Starch derivatives other than those mentioned above may also be used, for example aldehyde starches. Cellulose ethers, such as carboxymethylcellulose (Na salt), methylcellulose, hydroxyalkylcellulose, and mixed ethers, such as methylhydroxyethyl cellulose, methylhydroxypropylcellulose, methylcarboxymethylcellulose and mixtures thereof, can preferably be used, for example, in amounts of from 0.1 to 5 wt. %, based on the detergent.

It is preferred for the dye transfer inhibitor to be a polymer or a copolymer of cyclic amines such as vinylpyrrolidone and/or vinylimidazole. Polymers suitable as dye transfer inhibitors include polyvinylpyrrolidone (PVP), polyvinylimidazole (PVI), copolymers of vinylpyrrolidone and vinylimidazole (PVP/PVI), polyvinylpyridine-N-oxide, poly-N-carboxymethyl-4-vinylpyridium chloride, polyethylene glycol-modified copolymers of vinylpyrrolidone and vinylimidazole, and mixtures thereof. Particularly preferably, polyvinylpyrrolidone (PVP), polyvinylimidazole (PVI) or copolymers of vinylpyrrolidone and vinylimidazole (PVP/PVI) are used as dye transfer inhibitors. The polyvinylpyrrolidones (PVP) used preferably have an average molecular weight of from 2,500 to 400,000 and are commercially available from ISP Chemicals as PVP K 15, PVP K 30, PVP K 60 or PVP K 90, or from BASF as Sokalan® HP 50 or Sokalan® HP 53. The copolymers of vinylpyrrolidone and vinylimidazole (PVP/PVI) used preferably have a molecular weight in the range of from 5,000 to 100,000 g/mol. A PVP/PVI copolymer is commercially available from BASF under the name Sokalan® HP 56, for example. Other dye transfer inhibitors that can be extremely preferably used are polyethylene glycol-modified copolymers of vinylpyrrolidone and vinylimidazole, which are available from BASF under the name Sokalan® HP 66, for example.

The detergent is used in particular in the context of a washing process for textiles. The detergents described here are suitable, on the one hand, as washing aids which are used as textile pre-treatment and post-treatment agents in textile washing, i.e. agents with which the item of laundry is brought into contact before the actual washing, for example for dissolving stubborn soiling.

The detergent can be in a portion prepared for a wash cycle (e.g. as a water-soluble multi-chamber pouch) or in a multi-chamber storage container with a possible mixing chamber.

Within the meaning of the invention, a surfactant-containing liquor is a liquid preparation for treating a substrate that can be obtained by using the multi-component detergent of the present invention which has been diluted with at least one solvent (preferably water). Fabrics or textiles (such as clothing) can be used as substrates. The detergents according to the invention are preferably used to provide a surfactant-containing liquor for mechanical cleaning processes, as are carried out, for example, by a washing machine for textiles.

If it is a multi-component detergent, the further components of the multi-component detergent can be in any administration form established according to the prior art and/or in any expedient administration form. These include, for example, liquid, gel-like or pasty dosage forms. The container is preferably a pouch with two, three, four, five, six, seven or eight chambers, both in bulk packaging and also packaged in portions.

However, it is very particularly preferred according to the invention if the multi-component detergent comprises only liquid components, the liquid components preferably being packaged separately from one another by means of a wrapping.

In another particularly preferred embodiment, the multi-component detergent is a multi-component color detergent, in particular a liquid detergent, i.e. a textile detergent for colored textiles.

The detergents according to the invention preferably contain at least one alkalizing agent or the salt thereof in a total amount of from 1 to 20 wt. %, preferably 2 to 15 wt. %.

The total amount of the alkalizing agent and the salt thereof, or the total amount of all of the following preferred representatives, is calculated on the basis of the base form, i.e. if the alkalizing agent in the detergent according to the invention is (partly) in its salt form, the counterion is neglected in the amount calculation and only the base form without the absorbed proton is assumed for the salt portion.

The alkalizing agents are preferably selected from ($C_2$ to $C_6$) alkanolamine, sodium hydroxide, potassium hydroxide, sodium carbonate, sodium hydrogen carbonate or mixtures thereof.

According to the invention, the term ($C_2$ to $C_6$) alkanolamine is understood to mean organic amine compounds which have a carbon backbone of two to six carbon atoms to which at least one amino group (preferably exactly one amino group) and at least one hydroxyl group (again preferably exactly one hydroxyl group) bind.

Preferred ($C_2$ to $C_6$) alkanolamines according to the invention are primary amines.

In the context of the invention, it is preferred to use at least one ($C_2$ to $C_6$) alkanolamine with exactly one amino group. This is in turn preferably a primary amine.

The detergent according to the invention preferably contains at least one ($C_2$ to $C_6$)-alkanolamine selected from 2-aminoethan-1-ol (monoethanolamine), tris(2-hydroxyethyl)amine (triethanolamine), 3-aminopropan-1-ol, 4-Aminobutan-1-ol, 5-aminopentan-1-ol, 1-aminopropan-2-ol, 1-aminobutan-2-ol, 1-aminopentan-2-ol, 1-aminopentan-3-ol, 1-aminopentane 4-ol, 3-amino-2-methylpropan-1-ol, 1-amino-2-methylpropan-2-ol, 3-aminopropan-1,2-diol, 2-amino-2-methylpropan-1,3-diol (in particular under 2-aminoethan-1-ol, 2-amino-2-methylpropan-1-ol, 2-amino-2-methyl-propan-1,3-diol), or mixtures thereof. Monoethanolamine has proven to be a very particularly suitable ($C_2$ to $C_6$) alkanolamine as an alkalizing agent.

($C_2$ to $C_6$) alkanolamine or the salt thereof is particularly preferably present in a total amount of from 1 to 20 wt. %, preferably 2 to 15 wt. %, in the detergents according to the invention, in each case based on the basic form.

A third object of the invention is a further embodiment of the detergent according to the invention, namely a multi-component detergent, wherein at least one component is a detergent (in particular a liquid detergent) of the second object of the invention and at least one further additional component is selected from at least one composition selected from a liquid composition or a powder composition or granules.

According to the invention, the multi-component detergent is preferably located in a container (pouch) consisting of water-soluble material.

The container for said multi-component detergent comprises, in various embodiments, at least two spatially separate chambers (multi-chamber pouch), for example 2, 3, 4, 5, 6, 7 or 8 chambers. These chambers are separated from one another in such a way that the liquid or liquid and solid components of the detergent contained do not come into contact with one another. This separation can take place, for example, by a wall made of the same material as the container itself.

It is therefore particularly preferred according to the invention to package the multi-component detergent in a container consisting of water-soluble material with at least two separate chambers.

A material is water-soluble within the meaning of the present invention if, when stirred (stirring speed magnetic stirrer 300 rpm, stirring rod: 6.8 cm long, diameter 10 mm, beaker 1000 ml low form from Schott, Mainz) at 20° C., 0.1 g of the material dissolves in 800 ml water within 600 seconds in such a way that no solid particles of the material can be seen with the naked eye.

The water solubility of the material, in the form of a film, used for producing pouches for the wrapping can be determined by means of a square film of said material (film: 22×22 mm with a thickness of 76 μm) fixed in a square frame (edge length on the inside: 20 mm) according to the following measurement protocol. Said framed film is submerged into 800 ml of distilled water, temperature-controlled to 20° C., in a 1 liter beaker with a circular base (Schott, Mainz, beaker 1000 ml, low form), so that the surface of the tensioned film is arranged at a right angle to the base of the beaker, the upper edge of the frame is 1 cm below the water surface, and the lower edge of the frame is oriented in parallel with the base of the beaker such that the lower edge of the frame extends along the radius of the base of the beaker and the center of the lower edge of the frame is arranged above the center of the radius of the beaker bottom. The material should dissolve within 600 seconds when stirred (stirring speed magnetic stirrer 300 rpm, stirring rod: 6.8 cm long, diameter 10 mm), such that no solid film particles at all can be seen with the naked eye.

The water-soluble or water-dispersible material can comprise a polymer, a copolymer or mixtures thereof. Water-soluble polymers for the purposes of the invention are those polymers which are more than 2.5 wt. % soluble in water at room temperature.

Preferred water-soluble materials preferably comprise, at least in part, at least one substance from the group consisting of (acetalized) polyvinyl alcohol, polyvinyl pyrrolidone, polyethylene oxide, gelatin, polyvinyl alcohols substituted with sulphate, carbonate and/or citrate, polyalkylene oxides, acrylamides, cellulose esters, cellulose ethers, cellulose amides, cellulose, polyvinyl acetates, polycarboxylic acids and the salts thereof, polyamino acids or peptides, polyamides, polyacrylamides, copolymers of maleic acid and acrylic acid, copolymers of acrylamides and (meth)acrylic acid, polysaccharides, such as, for example, starch or guar derivatives, gelatin and, under the INCI names, Polyquaternium 2, Polyquaternium 17, Polyquaternium 18 and Polyquaternium 27. The water-soluble material is particularly preferably a polyvinyl alcohol.

In one embodiment of the invention, the water-soluble material comprises mixtures of different substances. Such mixtures allow the mechanical properties of the container to be adjusted and can influence the degree of water solubility.

The water-soluble material preferably contains at least one polyvinyl alcohol and/or at least one polyvinyl alcohol copolymer. "Polyvinyl alcohol" (abbreviated as PVAL or PVA and occasionally also as PVOH) is the designation for polymers having the general structure

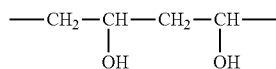

which also contain structural units in small proportions (approx. 2%) of the type

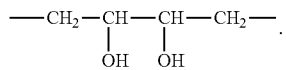

Commercially available polyvinyl alcohols, which are offered as a white-yellowish powder or granules with degrees of polymerization in the range of from approx. 100 to 2,500 (molar masses of from approx. 4,000 to 100,000 g/mol), have degrees of hydrolysis of from 98 to 99 mol. % or 87 to 89 mol. %, meaning they still contain residual acetyl groups. The manufacturers characterize the polyvinyl alcohols by indicating the degree of polymerization of the starting polymer, the degree of hydrolysis, the saponification number and the solution viscosity.

Depending on the degree of hydrolysis, polyvinyl alcohols are soluble in water and a few strongly polar organic solvents (formamide, dimethylformamide, dimethyl sulfoxide); they are not attacked by (chlorinated) hydrocarbons, esters, fats and oils. Polyvinyl alcohols are classified as toxicologically safe and are at least partially biodegradable. The water solubility can be reduced by post-treatment with aldehydes (acetalization), by complexing with Ni or Cu salts or by treatment with dichromates, boric acid or borax. The polyvinyl alcohol coatings are largely impervious to gases such as oxygen, nitrogen, helium, hydrogen and carbon dioxide, but allow water vapor to pass through. In preferred embodiments, the polyvinyl alcohols are substantially free of Ni and Cu salts and dichromates.

In the context of the present invention, it is preferable for the water-soluble material to comprise, at least in part, a polyvinyl alcohol of which the degree of hydrolysis is 70 to 100 mol. %, preferably 80 to 90 mol. %, particularly preferably 81 to 89 mol. %, and in particular 82 to 88 mol. %. In a preferred embodiment, the water-soluble material consists of at least 20 wt. %, particularly preferably at least 40 wt. %, very particularly preferably at least 60 wt. %, and in particular at least 80 wt. % of a polyvinyl alcohol of which the degree of hydrolysis is 70 to 100 mol. %, preferably 80 to 90 mol. %, particularly preferably 81 to 89 mol. %, and in particular 82 to 88 mol. %.

The polyvinyl alcohols described above are widely available commercially, for example under the trademark Mowiol® (Clariant). Polyvinyl alcohols which are particularly suitable in the context of the present invention are, for example, Mowiole 3-83, Mowiol® 4-88, Mowiol® 5-88, Mowiol® 8-88 and L648, L734, Mowiflex LPTC 221 ex KSE and the compounds from Texas Polymers such as Vinex 2034.

Preferred polyvinyl alcohol copolymers include, in addition to vinyl alcohol, dicarboxylic acids as further monomers. Suitable dicarboxylic acids are itaconic acid, malonic acid, succinic acid and mixtures thereof, with itaconic acid being preferred.

Polyvinyl alcohol copolymers which include, in addition to vinyl alcohol, an ethylenically unsaturated carboxylic acid, or the salt or ester thereof, are also preferred. Polyvinyl alcohol copolymers of this kind particularly preferably contain, in addition to vinyl alcohol, acrylic acid, methacrylic acid, acrylic acid ester, methacrylic acid ester or mixtures thereof.

The water solubility of polyvinyl alcohol polymer can be altered by post-treatment with aldehydes (acetalization) or ketones (ketalization). Polyvinyl alcohols which can be acetalized or ketalized with the aldehyde or keto groups of saccharides or polysaccharides or mixtures thereof have been found to be particularly preferred and, due to their decidedly good solubility in cold water, particularly advantageous.

Furthermore, the water solubility can be altered and thus set at desired values in a targeted manner by complexing with Ni or Cu salts or by treatment with dichromates, boric acid, or borax. These are preferably not contained. PVAL films are largely impervious to gases such as oxygen, nitrogen, helium, hydrogen and carbon dioxide, but allow water vapor to pass through.

Polymers selected from the group comprising acrylic acid-containing polymers, polyacrylamides, oxazoline polymers, polystyrene sulfonates, polyurethanes, polyesters, polyethers, polylactic acid, and/or mixtures of the above polymers may be added to the film material suitable as the water-soluble material in addition to polyvinyl alcohol.

Suitable water-soluble films for use as the water-soluble material of the water-soluble portion according to the invention are films which are sold by MonoSol LLC under the name Monosol M8630 or M8720. Other suitable films include films named Solublon® PT, Solublon® KA, Solublon® KC or Solublon® KL from Aicello Chemical Europe GmbH or the VF-HP films from Kuraray.

Preferred water-soluble materials are characterized in that they comprise hydroxypropyl methylcellulose (HPMC) which has a degree of substitution (average number of methoxy groups per anhydroglucose unit of the cellulose) of from 1.0 to 2.0, preferably from 1.4 to 1.9, and has a molar substitution (average number of hydroxypropoxy groups per anhydroglucose unit of the cellulose) of from 0.1 to 0.3, preferably from 0.15 to 0.25.

Polyvinylpyrrolidones, abbreviated as PVP, are produced by radical polymerization of 1-vinylpyrrolidone. Commercial PVPs have molar masses in the range of from approx. 2,500 to 750,000 g/mol and are offered as white, hygroscopic powders or as aqueous solutions.

Polyethylene oxides, PEOX for short, are polyalkylene glycols of general formula

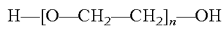

which are produced industrially by base-catalyzed polyaddition of ethylene oxide (oxirane) in systems mostly containing small amounts of water, with ethylene glycol as the starting molecule. They usually have molar masses in the range of from approx. 200 to 5,000,000 g/mol, corresponding to degrees of polymerization n of from approx. 5 to >100,000. Polyethylene oxides have an extremely low concentration of reactive hydroxy end groups and only show weak glycol properties.

Gelatin is a polypeptide (molar mass: approx. 15,000 to >250,000 g/mol) which is primarily obtained by hydrolysis of the collagen contained in the skin and bones of animals under acidic or alkaline conditions. The amino acid composition of the gelatin largely corresponds to that of the collagen from which it was obtained and varies depending on its provenance. The use of gelatin as a water-soluble coating material is extremely commonplace, particularly in pharmacy in the form of hard or soft gelatin capsules. In the form of films, gelatin is used only to a minor extent because of its high price in comparison with the above-mentioned polymers.

Preferred in the context of the present invention are water-soluble materials which comprise a polymer from the group of starch and starch derivatives, cellulose and cellulose derivatives, in particular methyl cellulose and mixtures thereof.

Starch is a homoglycan, with the glucose units being α-glycosidically linked. Starch is made up of two components of different molecular weights (MW): approx. 20 to 30% straight-chain amylose (MW approx. 50,000 to 150,000 g/mol) and 70 to 80% branched-chain amylopectin (MW approx. 300,000 to 2,000,000 g/mol). It also contains small amounts of lipids, phosphoric acid and cations. While the amylose forms long, helical, intertwined chains with approximately 300 to 1,200 glucose molecules due to the bond in the 1,4-position, the chain in amylopectin branches off after an average of 25 glucose units through 1,6 bonding with approximately 1,500 to 12,000 molecules of glucose. In addition to pure starch, starch derivatives which can be obtained from polymer-analogous reactions from starch are also suitable for producing water-soluble containers in the context of the present invention. Chemically modified starches of this type in this case encompass products of esterifications or etherifications in which hydroxy hydrogen atoms have been substituted. However, starches in which the hydroxy groups have been replaced by functional groups which are not bonded by an acid atom may also be used as starch derivatives. The group of starch derivatives includes, for example, alkali starches, carboxymethyl starch (CMS), starch esters and ethers and amino starches.

Pure cellulose has the formal gross composition ($C_6H_{10}O_5$) and is formally considered to be a β-1,4-polyacetal of cellubiose, which itself is composed of two glucose molecules. In this case, suitable celluloses consist of from approx. 500 to 5,000 glucose units and therefore have an average molar mass of from 50,000 to 500,000. Cellulose derivatives which can be obtained from cellulose by polymer-like reactions may also be used as cellulose-based disintegration agents in the scope of the present invention. Chemically modified celluloses of this type in this case encompass products of esterifications or etherifications in which hydroxy hydrogen atoms have been substituted. However, celluloses in which the hydroxy groups have been replaced by functional groups which are not bonded by an acid atom may also be used as cellulose derivatives. The group of cellulose derivatives includes, for example, alkali celluloses, carboxymethyl cellulose (CMC), cellulose esters and ethers as well as amino celluloses.

The water-soluble material can have other additives. These are, for example, plasticizers, such as dipropylene glycol, ethylene glycol or diethylene glycol, water or disintegrating agents.

Polyvinyl alcohol is particularly preferably used as the water-soluble material. On the one hand, this is easy to process and inexpensive to maintain. In addition, it is particularly soluble in water and thus allows the produced container to be used in a variety of ways.

A particularly preferred multi-component detergent according to the invention is characterized in that the multi-component detergent is in the form of a multi-chamber pouch, in particular with a water-soluble film, particularly preferably based on polyvinyl alcohol.

In addition, preferred multi-component detergents preferably contain a bitter principle, and the bitter principle is particularly preferably contained in the detergent and/or in the container of the multi-component detergent, in particular in the film.

It is preferred according to the invention if at least one bitter principle is contained in the water-soluble material to increase product safety.

Preferred bitter principles have a bitter value of at least 1,000, preferably at least 10,000, particularly preferably at least 200,000. To determine the bitter value, the standardized method described in European Pharmacopoeia (5th main edition, Stuttgart 2005, Volume 1 General Part Monograph Groups, 2.8.15 Bitter value, p. 278) is used. An aqueous solution of quinine hydrochloride, the bitter value of which is fixed at 200,000, serves as a comparison. This means that 1 gram of quinine hydrochloride makes 200 liters of water bitter. The inter-individual taste differences in the organoleptic test for bitterness are compensated for by a correction factor.

Very particularly preferred bitter principles are selected from denatonium benzoate, glycosides, isoprenoids, alkaloids, amino acids and mixtures thereof, particularly preferably denatonium benzoate.

Glycosides are organic compounds of the general structure R—O—Z, in which an alcohol (R—OH) is linked to a sugar part (Z) via a glycosidic bond.

Suitable glycosides are, for example, flavonoids such as quercetin or naringin or iridoid glycosides such as aucubin and in particular secoiridoid, such as amarogentin, dihydrofoliamentin, gentiopicroside, gentiopikrin, swertiamarin, sweroside, gentioflavoside, centauroside, methiafolin, harpagoside and centapikrin, sailicin or condurangin.

Isoprenoids are compounds that are formally derived from isoprene. Examples are in particular terpenes and terpenoids.

Suitable isoprenoids include, for example, sequiterpene lactones such as absinthin, artabsin, cnicin, lactucin, lactucopikrin or salonitenolide, monoterpene ketones (thujones) such as, for example α-thujone or β-thujone, tetranortriterpenes (limonoids) such as deoxylimones, desoxylimonic acid, limonin, ichangin, iso-obacunonic acid, obacunone, obacunonic acid, nomilin or nomilic acid, terpenes such as marrubin, premarrubin, carnosol, carnosolic acid or quassin.

Alkaloids refer to naturally occurring, chemically heterogeneous, mostly alkaline, nitrogen-containing organic compounds of secondary metabolism that act on the animal or human organism.

Suitable alkaloids are, for example, quinine hydrochloride, quinine hydrogen sulfate, quinine dihydrochloride, quinine sulfate, columbine and caffeine.

Suitable amino acids include, for example, threonine, methionine, phenylalanine, tryptophan, arginine, histidine, valine and aspartic acid.

Particularly preferred bitter principles are quinine sulfate (bitter value=10,000), naringin (bitter value=10,000), sucrose octaacetate (bitter value=100,000), quinine hydrochloride, denatonium benzoate (bitter value>100,000,000) and mixtures thereof, very particularly preferably denatonium benzoate (e.g. available as Bitrex®).

The water-soluble material preferably contains, based on its total weight, bittering agents (particularly preferably denatonium benzoate) in a total amount of at most 1 part by weight of bitter principle to 250 parts by weight of the water-soluble material (1:250), particularly preferably at most 1:500, very particularly preferably at most 1:1,000.

It is preferable to use the detergent according to the invention or multi-component detergent according to the invention for washing textiles, in particular for removing bleachable soiling, very particularly preferably for removing soiling based on constituents and residues of deodorants, rust, berries, tea and red wine.

Methods for cleaning textiles are generally characterized in that, in a plurality of method steps, various cleaning-active substances are applied to the material to be cleaned and washed off after the exposure time, or in that the material to be cleaned is otherwise treated with a detergent or a solution of the detergent.

A fourth object of the invention is therefore a method for washing textiles, comprising the steps of
- adding a detergent of the second object or a multi-component detergent of the third object to a fabric or textile; and carrying out a washing procedure, preferably in a washing machine.

Preferred is a method for textile treatment comprising the method steps of
(a) providing an aqueous liquor by mixing 0.5 liters to 40.0 liters of water with 0.5 to 100 g of a detergent of the second object of the invention, and
(b) bringing a textile into contact with the aqueous liquor prepared according to (a).

It is preferred if in step (b) the textile is in contact with the aqueous liquor prepared according to (a) for 10 to 240 minutes, in particular 20 to 180 minutes.

It is further preferred if the textile is rinsed and dried after step (b).

It is particularly preferred to carry out the method in an automatic washing machine. Before step (a), the textile is placed in the drum of the washing machine. A detergent of the second or third object of the invention is poured into the detergent container of the washing machine or added to the drum of the washing machine together with the textiles. It is preferred to add the multi-component detergent of the third object of the invention into the drum of the washing machine.

0.5 to 40 liters of water is then added and mixed. Remarkably, the textile is not dyed by the catechol metal complex compound according to the invention. This applies even if the detergent or multi-component detergent according to the invention is dosed into the drum of the washing machine and comes into direct contact with the textile.

In order to prepare said solution, it is preferred according to the invention for 10 to 110 g, in particular 15 to 100 g of the detergent of the second object of the invention to be mixed with 5 to 25 l water, in particular with 10 to 20 l water.

In the methods described, temperatures of 60° C. or less, for example 50° C. or less, are used in different embodiments of the invention. These temperature specifications relate to the temperatures used in step (b).

As already mentioned, the soiling can be pretreated with the detergent according to the invention prior to the actual washing process and/or initially a surfactant-containing liquor is provided as a washing solution which contains the (multi-component) detergent according to the invention and which is subsequently brought into contact with the textile to be cleaned.

All of the embodiments described herein in connection with the detergents of the invention, in particular with regard to the specification of the ingredients, are equally applicable to the methods and uses described and vice versa.

EXAMPLES 1.0 Preparation and Isolation of the Colored Complexes with N,N'-Dipropyl-2,3-dihydroxyterephthaldiamide (Ligand L)

0.3 mmol of N,N'-dipropyl-2,3-dihydroxyterephthaldiamide (ligand L) was dissolved in 10 ml of methanol. 0.3 mmol of KOH (as a 0.5M solution in methanol) was added to this with stirring. 0.1 mmol of the metal(III) chloride or 0.15 mmol of the metal(II) chloride was dissolved in 4 ml of methanol. This solution was then added to the first solution. After a stirring time of one hour, the resulting solution was concentrated to 4 ml and then 50 ml diethyl ether was added. The precipitated metal complex was isolated by filtration.

Colored powders of the following metal complexes Fe(III)L$_3$ (red), Ce(III)L$_3$ (violet) and Mn(II)L$_2$ (green) were produced in this way.

From a spatula tip of a dye, a solution for each dye and pH at pH 8, pH 9.5 and pH 10 was prepared with pH adjustment using NaOH. An increase in the pH of the respective solutions did not lead to any visible change in color.

UV/VIS spectra of the complexes Fe(III)L$_3$ (red), Ce(III)L$_3$ (violet) and Mn(II)L$_2$ (green) were recorded in aqueous solution at pH 8 (NaOH) and 20° C.

TABLE 1

| Maxima in the UV/VIS spectrum at a wavelength between 400 and 800 nm | |
|---|---|
| Catechol metal complex | Maximum (wavelength in nm) |
| Fe(III)L$_3$ | 444 (shoulder 495) |
| Ce(III)L$_3$ | 531 |
| Mn(II)L$_2$ | 626 |

2.0 Preparation of Detergents According to the Invention

The following detergents according to the invention according to Table 2 were prepared with stirring.

TABLE 2

| Liquid detergent | F1 [wt. %] | F2 [wt. %] | F3 [wt. %] | F4 [wt. %] | F5 [wt. %] | F6 [wt. %] |
|---|---|---|---|---|---|---|
| $C_{11-13}$ alkylbenzene sulfonic acid | 22.0 | 26.0 | 22.0 | 26.0 | 9.0 | 3.0 |
| ($C_{12-14}$) fatty alcohol ether sulfate having 2 units of ethylene oxide | — | — | — | — | 9.0 | 4.6 |
| $C_{13-15}$ alkyl alcohol branched at the 2-position, ethoxylated with 8 mol ethylene oxide | 24.0 | 27.0 | 24.0 | 27.0 | 6.0 | — |
| Fatty alcohol ether ethoxylated with 7 mol ethylene oxide | — | — | — | — | — | 3.7 |
| Glycerol | 10.5 | 9.0 | 10.5 | 9.0 | — | — |
| 2-aminoethanol | 6.0 | 6.8 | 6.0 | 6.8 | — | — |
| Sodium hydroxide | — | — | — | — | 4.0 | 0.6 |
| Ethoxylated polyethyleneimine | 6.0 | 5.0 | 6.0 | 5.0 | — | — |
| $C_{12-18}$ fatty acid | 7.5 | 7.5 | 7.5 | 7.5 | 1.0 | 1.3 |
| Diethylenetriamine-N,N,N',N',N''-penta(methylenephosphonic acid), heptasodium salt | 0.7 | 0.6 | 0.7 | 0.6 | 3.0 | 0.2 |
| Citric acid | — | — | — | — | To pH 8.5 | To pH 8.5 |
| Boric acid | — | — | — | — | 1.0 | 0.5 |
| 1,2-propylene glycol | 8.2 | 4.5 | 8.2 | 4.5 | 2.0 | 0.5 |
| Ethanol | 3.0 | 4.0 | 3.0 | 4.0 | 1.0 | 0.2 |
| Sodium bisulfite | — | 0.1 | — | 0.1 | — | — |
| Denatonium benzoate | 0.001 | 0.001 | 0.001 | 0.001 | 0.001 | 0.001 |
| Soil-release polymers of ethylene terephthalate and polyethylene oxide terephthalate | 1.4 | 1.0 | 1.4 | 1.0 | 0.5 | — |
| Sokalan HP 56 | — | 0.1 | — | 0.1 | 0.2 | — |
| Optical brightener | 0.6 | — | 0.6 | — | — | — |
| Perfume | 1.7 | 1.7 | 1.7 | 1.7 | 2.6 | 1.0 |
| Protease, amylase, lipase, cellulase | 0.8 | 0.8 | 0.8 | 0.8 | 1.0 | 1.0 |
| Fe(III)L$_3$ | 0.015 | 0.015 | — | — | 0.015 | — |
| Mn(II)L$_2$ | — | — | 0.05 | 0.05 | — | 0.05 |
| Water | to make up to 100 | to make up to 100 | to make up to 100 | to make up to 100 | to make up to 100 | to make up to 100 |

Formulations F1 to F6 were stored at 5° C., 21° C. and 40° C. for 4 weeks each. The compositions were storage-stable and, compared to the starting product, had no discoloration discernible to the naked eye before storage.

3.0 Washing Tests

In addition, washing tests were carried out with detergents F1 and F3 in Table 2 in accordance with the following test conditions.

White fabrics (WFK 10A, WFK 20A and WFK 30A) were washed in a Miele washing machine type 318 at 16° d and 40° C. in a short program twice in succession with 35 g of powder detergent from the commercial product "Weißer Riese Universal." A wash cycle without detergent was then carried out. Fabric WFK 10 A is designated by "wfk Testgewebe GmbH" as "standard cotton," WFK 20A is designated as "polyester/cotton (65%/35%)" and WFK 30A is designated as "polyester."

The prewashed, white fabrics (WFK 10A, WFK 20A and WFK 30A) as described above were washed in addition to 23 white hand towels, 5 white terry towels and 6 white T-shirts (total washing load 3 kg) with 25 g of the corresponding formulation according to the invention in Table 2 in a Miele washing machine type 318 at 16° d and 40° C. for 60 minutes in the main wash cycle, then rinsed and hung to dry. This procedure was carried out 3 times in a row.

The white fabrics showed no discoloration and no staining. This demonstrates that the catechol metal complex used according to the invention does not stain the textile even with repeated washing.

What is claimed is:

1. A detergent containing, in each case based on the total weight of the detergent in a total amount from 0.001 to 10.0 wt. % at least one catechol metal complex compound of formula (I)

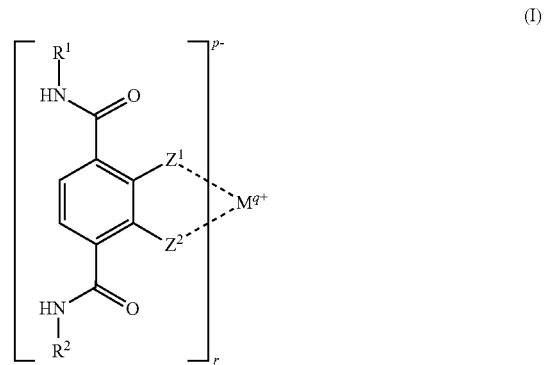

where $R^1$ and $R^2$ independently represent a hydrocarbon group having 1 to 20 carbon atoms, which is optionally substituted by at least one group selected from hydroxy, $(C_1-C_4)$ alkoxy, $(C_1-C_4)$ alkoxy$(CH_2CH_2O)_n$—, —NR'R'' or —N$^+$R'R''R'''X$^-$, where n=1 to 10, R', R'' and R''' independently represent H or a linear or branched aliphatic hydrocarbon group having 1 to 3 carbon atoms and $X^-$ represents an anion, $Z^1$ and $Z^2$ independently represent OH or $O^-$, M represents a metal cation of a transition metal or lanthanoid, q as the charge number of the metal cation M represents a number 2, 3 or 4, as the charge number of the catechol ligand represents a number 0, 1 or 2, r represents a number 1, 2, 3 or 4, and at least one surfactant in a total amount from 2 to 70 wt. %.

2. The detergent according to claim 1 wherein, in formula (I) the groups $R^1$ and $R^2$ independently represent an alkyl group, an alkoxyalkyl group, a hydroxyalkyl group, a hydroxyalkyloxyalkyl group, (N-hydroxyethyl)-aminoethyl, (N-methoxyethyl)-aminoethyl or (N-ethoxyethyl)-aminoethyl, or an aromatic group.

3. The detergent according to claim 2 wherein, in formula (I) the groups $R^1$ and $R^2$ independently represent an alkyl group, an alkoxyalkyl group, a hydroxyalkyl group, a hydroxyalkyloxyalkyl group, (N-hydroxyethyl)-aminoethyl, (N-methoxyethyl)-aminoethyl, (N-ethoxyethyl)-aminoethyl, methyl, ethyl, n-propyl, isopropyl, n-butyl, sec-butyl, tert-butyl, iso-butyl, n-pentyl, iso-pentyl, neopentyl, hexyl, 2-hydroxyethyl, 2-hydroxypropyl, 3-hydroxypropyl, 2-methoxyethyl, 2-ethoxyethyl, 3-methoxypropyl, 3-ethoxypropyl, (N-hydroxyethyl)-aminoethyl, or phenyl.

4. The detergent according to claim 1 wherein, in formula (I) the groups $R^1$ and $R^2$ are the same.

5. The detergent according to claim 1 wherein, in formula (I) M is selected from Fe, Mn, Cr, Ni, Co, Ce, Cu or hydrates of these metal ions.

6. The detergent according to claim 1 wherein, in formula (I) M represents a metal cation of a transition metal or a metal cation from Ti, Zr, Hf, V, Nb, Ta, Cr, Mo, W, Mn, Fe, Ru, Co, Ni, Cu, Zn, Ce or Sm.

7. The detergent according to claim 1, wherein the detergent has a pH at 20° C. from 6 to 11.5.

8. The detergent according to claim 1, wherein the at least one surfactant comprises anionic surfactant and/or nonionic surfactant.

9. The detergent according to claim 1, wherein the catechol metal complex compound of formula (I) absorbs light in a wavelength from 400 to 800 nm, measured by means of a two-beam spectrophotometer at a concentration of the complex of $10^{-5}$ mol/L in water at 20° C., a pH of 8 and a layer thickness of 1 cm.

10. The detergent according to claim 1, wherein the detergent additionally contains at least one free catechol compound of formula (II) or the salt thereof

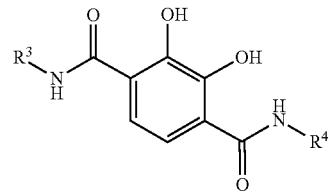

where $R^3$ and $R^4$ independently represent a hydrocarbon group having 1 to 20 carbon atoms, which is optionally substituted by at least one group selected from hydroxy, $(C_1-C_4)$ alkoxy, $(C_1-C_4)$ alkoxy$(CH_2CH_2O)_n$—, —NR'R" or —N$^+$R'R"R'''$X^-$, where n=1 to 10, R', R" and R''' independently represent H or a linear or branched aliphatic hydrocarbon group having 1 to 3 carbon atoms and $X^-$ represents an anion, with the proviso that the catechol compound of formula (II) and the salt thereof are different from compounds of formula (I).

11. The detergent according to claim 10, wherein the detergent contains the at least one free catechol compound of formula (II) in a total amount from 0.01 to 10.0 wt. %.

12. The detergent, according to claim 1, wherein the detergent is a liquid detergent.

13. A multi-component detergent, wherein at least one component is a detergent according to claim 1 and at least one further additional component is selected from at least one composition selected from a liquid composition or a powder composition or granules.

14. The multi-component detergent according to claim 13, wherein the multi-component detergent is in the form of a multi-chamber pouch.

15. The multi-component detergent according to claim 14, wherein the multi-component detergent is in the form of a multi-chamber pouch made of a water-soluble film.

16. The multi-component detergent according to claim 13, wherein the multi-component detergent contains a bittering agents, and the bittering agents is contained in the detergent and/or in the container of the multi-component detergent.

17. The multi-component detergent according to claim 13, wherein the detergent is a liquid detergent.

18. A method for washing textiles, comprising the steps of adding a detergent, according to claim 1, to a fabric or textile; and carrying out a washing procedure.

* * * * *

UNITED STATES PATENT AND TRADEMARK OFFICE
CERTIFICATE OF CORRECTION

PATENT NO. : 11,560,532 B2
APPLICATION NO. : 17/228524
DATED : January 24, 2023
INVENTOR(S) : Frank Meier et al.

It is certified that error appears in the above-identified patent and that said Letters Patent is hereby corrected as shown below:

In the Specification

Column 9, Line 53 change "$C_{12}$-14" to --$C_{12-14}$--.
Column 9, Line 55 change "$C_{12}$-18" to --$C_{12-18}$--.
Column 14, Line 29 change "1 to 100" to --1 to 100 μm--.
Column 14, Line 30 change "5 to 95" to --5 to 95 μm--.
Column 14, Line 30 change "10 to 90" to --10 to 90 μm--.
Column 20, Line 4 change "Rockford, Ill" to --Rockford, IL--.
Column 24, Line 20 change "4,4'"' to --4,4'--.
Column 24, Line 21 change "2,2'"' to --2,2'--.
Column 26, Line 33 change "methylhydroxyethyl cellulose" to --methylhydroxyethylcellulose--.

In the Claims

Column 37, Line 9 change "as the charge" to --p as the charge--.

Signed and Sealed this
Ninth Day of January, 2024

Katherine Kelly Vidal
*Director of the United States Patent and Trademark Office*